United States Patent
Lee et al.

(10) Patent No.: US 12,016,665 B2
(45) Date of Patent: Jun. 25, 2024

(54) METHOD FOR GENERATING HEART RATE VARIABILITY INFORMATION RELATED TO EXTERNAL OBJECT BY USING PLURALITY OF FILTERS, AND DEVICE THEREFOR

(71) Applicant: SAMSUNG ELECTRONICS CO., LTD., Suwon-si (KR)

(72) Inventors: Wonkyu Lee, Suwon-si (KR); Hwan Shim, Suwon-si (KR); Hyunsu Kim, Suwon-si (KR); Yongjin Lee, Suwon-si (KR); Dawoon Jung, Suwon-si (KR); Seounghun Kim, Suwon-si (KR); Taeho Kim, Suwon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 923 days.

(21) Appl. No.: 16/967,970

(22) PCT Filed: Jan. 31, 2019

(86) PCT No.: PCT/KR2019/001386
§ 371 (c)(1),
(2) Date: Aug. 6, 2020

(87) PCT Pub. No.: WO2019/156433
PCT Pub. Date: Aug. 15, 2019

(65) Prior Publication Data
US 2021/0361179 A1    Nov. 25, 2021

(30) Foreign Application Priority Data
Feb. 7, 2018   (KR) .................... 10-2018-0015272

(51) Int. Cl.
*A61B 5/00* (2006.01)
*A61B 5/024* (2006.01)
(Continued)

(52) U.S. Cl.
CPC .......... *A61B 5/02405* (2013.01); *A61B 5/721* (2013.01); *A61B 5/7246* (2013.01);
(Continued)

(58) Field of Classification Search
CPC ... A61B 5/02405; A61B 5/721; A61B 5/7246; A61B 5/725; A61B 5/02416;
(Continued)

(56) References Cited

U.S. PATENT DOCUMENTS

| 6,905,470 B2 | 6/2005 | Lee et al. |
| 7,186,220 B2 | 3/2007 | Stahmann et al. |

(Continued)

FOREIGN PATENT DOCUMENTS

| CN | 103222283 | 7/2013 |
| CN | 106687027 | 5/2017 |

(Continued)

OTHER PUBLICATIONS

Extended European Search Report dated Dec. 17, 2020 in counterpart European Application No. 19751774.1.
(Continued)

*Primary Examiner* — Carl H Layno
*Assistant Examiner* — Anh-Khoa N Dinh
(74) *Attorney, Agent, or Firm* — Nixon & Vanderhye, P.C.

(57) ABSTRACT

An example electronic device may include a detection circuit and a processor operatively connected to the detection circuit. The processor may be configured to obtain a first signal associated with an external object through the detection circuit; obtain a first HR, using a first filter having an attribute of a first frequency band; obtain a second HR, using a second filter having an attribute of a second frequency band, based at least on the first signal; change at least some attributes associated with the second filter, based at least on
(Continued)

the first HR and the second HR; obtain a second signal associated with the external object through the detection circuit; and generate heart rate variability (HRV) information, using the second filter, in which the at least some attributes are changed, based on the second signal.

13 Claims, 19 Drawing Sheets

(51) Int. Cl.
  *G16H 40/67* (2018.01)
  *G16H 50/30* (2018.01)
  *G16H 50/70* (2018.01)
(52) U.S. Cl.
  CPC .............. *A61B 5/725* (2013.01); *G16H 40/67* (2018.01); *G16H 50/30* (2018.01); *G16H 50/70* (2018.01); *A61B 5/02416* (2013.01)
(58) Field of Classification Search
  CPC . A61B 5/02444; A61B 5/7225; A61B 5/0245; A61B 5/0205; A61B 5/024; A61B 5/346; A61B 5/352; A61B 5/4094; A61B 5/7275; A61B 5/746; A61B 5/0816; A61B 5/021; A61B 5/026; A61B 5/053; A61B 5/318; A61B 5/349; A61B 5/363; A61B 5/4824; A61B 5/4836; A61B 5/686; A61B 5/02438; A61B 5/0295; A61B 5/0535; A61B 5/11; A61B 5/1135; A61B 5/14542; A61B 5/14551; A61B 5/4818; A61B 5/6804; A61B 5/681; A61B 5/7264; A61B 5/7278; G16H 40/67; G16H 50/30; G16H 50/70; A61N 1/36064; A61N 1/0534; A61N 1/36062; A61N 1/36071; A61N 1/36139; A61N 1/36514; A61N 1/36578; A61N 1/36592; A61N 1/37247; A61N 1/37264
  See application file for complete search history.

(56) References Cited

U.S. PATENT DOCUMENTS

| | | |
|---|---|---|
| 8,585,607 B2 | 11/2013 | Klap et al. |
| 9,055,377 B2 | 6/2015 | Kinsbergen et al. |
| 9,872,652 B2 | 1/2018 | Salehizadeh et al. |
| 10,238,351 B2 | 3/2019 | Halperin et al. |
| 10,743,818 B2 | 8/2020 | Brouse |
| 11,766,220 B2 | 9/2023 | Brouse |
| 2003/0212336 A1 | 11/2003 | Lee et al. |
| 2005/0004609 A1 | 1/2005 | Stahmann et al. |
| 2008/0275349 A1 | 11/2008 | Halperin et al. |
| 2010/0145171 A1 | 6/2010 | Park et al. |
| 2011/0046498 A1 | 2/2011 | Klap et al. |
| 2012/0203080 A1 | 8/2012 | Kim et al. |
| 2012/0302897 A1* | 11/2012 | Chen ...................... G16H 40/67 705/2 |
| 2013/0150766 A1 | 6/2013 | Olde et al. |
| 2014/0018635 A1* | 1/2014 | Buchheim .............. A61B 5/725 600/301 |
| 2015/0190062 A1 | 7/2015 | Han et al. |
| 2016/0058376 A1 | 3/2016 | Baek et al. |
| 2016/0166197 A1 | 6/2016 | Venkatraman et al. |
| 2016/0361021 A1 | 12/2016 | Salehizadeh et al. |
| 2017/0181680 A1 | 6/2017 | Baek et al. |
| 2017/0188864 A1 | 7/2017 | Drury |
| 2017/0231576 A1 | 8/2017 | Yamaji |
| 2019/0254590 A1 | 8/2019 | Venkatraman et al. |
| 2020/0077952 A1 | 3/2020 | Baek et al. |

FOREIGN PATENT DOCUMENTS

| | | |
|---|---|---|
| CN | 107088060 | 8/2017 |
| JP | 2003-310562 | 11/2003 |
| JP | 2012-502671 | 2/2012 |
| KR | 10-2010-0065084 | 6/2010 |
| KR | 10-0997444 | 11/2010 |
| KR | 10-2016-0028351 | 3/2016 |
| KR | 10-2017-0076329 | 7/2017 |
| KR | 10-2017-0136727 | 12/2017 |

OTHER PUBLICATIONS

Office Action dated Jan. 18, 2023 in EP Application No. 19751774.1.
International Search Report for PCT/KR2019/001386 dated May 16, 2019, 6 pages.
Written Opinion of the ISA for PCT/KR2019/001386 dated May 16, 2019, 4 pages.
Office Action dated Aug. 29, 2023 in Chinese Application No. 201980012456.0 and English-language translation.

* cited by examiner

METHOD FOR GENERATING HEART RATE VARIABILITY INFORMATION RELATED TO EXTERNAL OBJECT BY USING PLURALITY OF FILTERS, AND DEVICE THEREFOR

This application is the U.S. national phase of International Application No. PCT/KR2019/001386 filed Jan. 31, 2019 which designated the U.S. and claims priority to KR Patent Application No. 10-2018-0015272 filed Feb. 7, 2018, the entire contents of each of which are hereby incorporated by reference.

BACKGROUND

Field

Embodiments disclosed in this specification relate to information processing technology associated with an external object.

Description of Related Art

Types of healthcare are variously developed. Research on an electronic device that enables users to continuously monitor biometric information and to manage health of the users during daily life is on the way.

The electronic device (e.g., a wearable device worn on a wrist, such as a smart watch or a smart band) may extract and provide heart rate (HR) information based on the principle of photoplethysmography (PPG).

As blood vessels expand and contract repeatedly whenever a heart beats, blood flow in arteries is changed. When a light emitting diode (LED) light is irradiated to human tissue and then the light transmitted or reflected is collected by a photodiode, a PPG signal in the form of a periodic pulse, to which the change in blood flow is reflected, may be measured. The number of pulses per second may be determined and HR may be extracted, based on a method for detecting a peak to peak interval (PPI) of the PPG signal. Furthermore, an elaborately-recorded PPI may be used to grasp the interaction of sympathetic and parasympathetic nerves and the regulation of a cardiovascular function by estimating heart rate variability (HRV).

SUMMARY

The availability of a method for extracting a heart beat interval based on the method for detecting the PPI of a PPG signal to estimate the HR and the HRV may not be high in an environment with user movement. For example, when various noises including a motion occurring in daily life is included in the PPG signal measured by an optical sensor, the waveform may be distorted or the periodicity may disappear, and thus it may be difficult to detect PPI with the conventional method.

Even when various noises are included, a HR monitoring method based on frequency analysis of a PPG signal and frequency power tracking of HR generation band is designed to stably detect HR. However, because peak detection is required to estimate the heart beat interval, it still has limitations that may not reproduce a sophisticated HRV based on PPI.

In a situation where a lot of motions are involved using the conventional method, obtaining the heart beat interval using an electronic device or obtaining various biometric information processing results using the heart beat interval may reduce the accuracy of the algorithm using data and biometric information. Hereinafter, in the embodiment disclosed in the specification, it is possible to suggest a method for efficiently processing information associated with an external object even when there is a motion of the external object (e.g., a user), and a device therefor.

According to an embodiment disclosed in this specification, an electronic device may include a detection circuit and a processor operatively connected to the detection circuit. The processor may be configured to obtain a first signal associated with an external object through the detection circuit, to obtain a first heart rate (HR), using a first filter having an attribute of a first frequency band and to obtain a second HR, using a second filter having an attribute of a second frequency band, based at least on the first signal, to change at least some attributes associated with the second filter, based at least on the first HR and the second HR, and to obtain a second signal associated with the external object through the detection circuit, and generate heart rate variability (HRV) information, using the second filter, in which the at least some attributes are changed, based on the second signal. According to an embodiment, the first filter may use the first signal processing scheme and the second filter may use the second signal processing scheme.

Furthermore, according to an embodiment disclosed in this specification, a method performed by an electronic device may include obtaining a signal associated with an external object, obtaining a first HR based on the signal, using a first signal processing scheme, obtaining a second HR based on the signal, using a second signal processing scheme, and generating HRV information based at least on the second HR.

According to embodiments disclosed in the specification, an electronic device may more accurately obtain the result of processing information associated with an external object.

According to embodiments disclosed in the specification, an electronic device may efficiently process information associated with an external object.

Besides, a variety of effects directly or indirectly understood through the disclosure may be provided.

BRIEF DESCRIPTION OF THE DRAWINGS

With regard to description of drawings, the same or similar components may be marked by the same or similar reference numerals.

DETAILED DESCRIPTION

Hereinafter, various embodiments of the disclosure will be described with reference to accompanying drawings. However, those of ordinary skill in the art will recognize that modification, equivalent, and/or alternative on various embodiments described herein may be variously made without departing from the scope and spirit of the disclosure.

Figure 1:
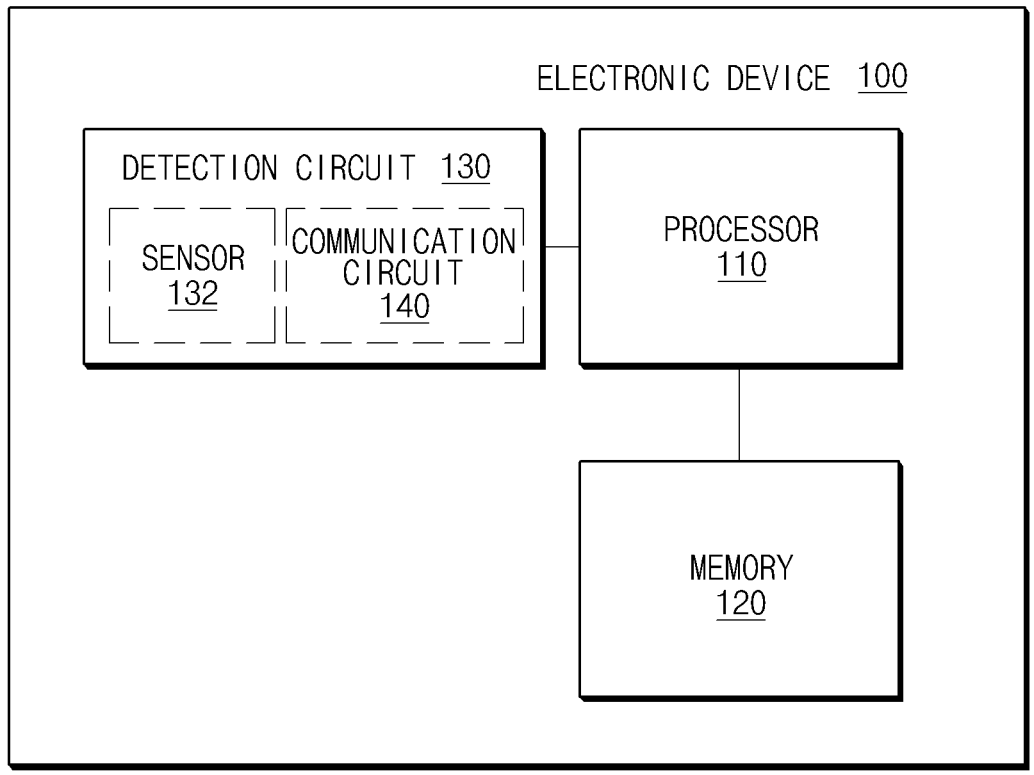
FIG. 1 is a block diagram illustrating a configuration of an electronic device, according to an embodiment.

FIG. 1 is a block diagram illustrating a configuration of an electronic device, according to an embodiment.

According to an embodiment, an electronic device 100 (e.g., an electronic device 1901 of FIG. 19) may include at least one of a processor 110 (e.g., a processor 1920 of FIG. 19), a memory 120 (e.g., a memory 1930 of FIG. 19), or a detection circuit 130. In various embodiments, the electronic device 100 may omit a part of the above-mentioned components or may further include other components. For example, a configuration such as a display (e.g., a display device 1960 in FIG. 19), a camera (e.g., a camera module 1980 in FIG. 19), a battery, or an input/output interface (e.g., an interface 1977 in FIG. 19) may be additionally included in the electronic device 100.

According to an embodiment, the processor 110 may perform operations according to various embodiments disclosed in the specification. For example, the processor 110 may process information associated with an external object. For example, the external object may be a user. The information associated with the external object may include biometric information. For example, the electronic device may process information associated with an external object and may obtain heart beat information (e.g., HR or HRV). The processor 110 may display heart beat information. According to an embodiment, the processor 110 may be disposed in the housing of the electronic device 100. The processor 110 may be electrically or operatively connected to the memory 120 and the detection circuit 130. The processor 110 may execute instructions stored in the memory 120.

According to an embodiment, the memory 120 may store at least one application or data associated with the operation of the electronic device 100. According to an embodiment, the memory 120 may store an application program associated with a user's biometric information, such as health or sleep patterns. According to various embodiments, the memory 120 may include instructions for various operations disclosed in the specification. The instructions may be executed by the processor 110.

According to an embodiment, the electronic device 100 may obtain a signal associated with an external object. To this end, the electronic device 100 may include the detection circuit 130. According to an embodiment, the detection circuit 130 may include at least one of a sensor 132 (e.g., a sensor module 1976 of FIG. 19) or a communication circuit 140 (e.g., a communication module 1990 of FIG. 19).

The signal associated with the external object may include, for example, a biometric signal and/or a motion signal. The biometric signal may be a signal associated with the user's biometric activity. The motion signal may be a signal indicating the user's motion, for example, an acceleration signal.

According to an embodiment, the sensor 132 may obtain the signal associated with an external object. The signal associated with the external object may include a sensing signal. For example, the sensor 132 may include at least one of a biometric sensor (e.g., a photo-plethysmography (PPG) sensor) for measuring a biometric signal or a motion sensor (e.g., an accelerometer (ACC) sensor) for measuring a motion signal such as acceleration. In addition, the sensor 132 according to various embodiments may include various devices (e.g., an electrocardiography (ECG) sensor, a gyro sensor, a barometric sensor, or the like) for measuring a biometric signal or a motion signal of the user.

According to an embodiment, the PPG sensor may include at least one light emitting unit and at least one light receiving unit. The light receiving unit may obtain light, which is transmitted or reflected through the user's skin, among the light output from the light-emitting unit, and may deliver a biometric signal corresponding to the obtained light to the processor. In the following description, the sensing signal obtained by the PPG sensor may be referred to as a PPG signal.

According to an embodiment, the acceleration sensor may obtain a motion signal of the electronic device 100. For example, when the electronic device 100 measures a biometric signal of the user using a PPG sensor, the acceleration sensor may obtain a motion signal and may deliver the obtained motion signal to the processor. In the following description, the signal obtained by the acceleration sensor may be referred to as an accelerometer (ACC) signal.

According to an embodiment, the electronic device 100 may obtain a signal associated with an external object from an external device. According to an embodiment, the electronic device 100 may transmit or receive a signal associated with the external object to or from the external device through the communication circuit 140. At this time, the signal associated with the external object may be a signal obtained by a sensor of an external electronic device. For example, the signal associated with the external object may be a biometric signal or a motion signal. According to an embodiment, the communication circuit 140 may support wired communication or wireless communication. The wireless communication may include short-range communication or long-range communication.

According to an embodiment, the electronic device 100 may include a display. The electronic device 100 may display heart beat information associated with an external object obtained according to an embodiment disclosed later, on the display.

Figure 2:
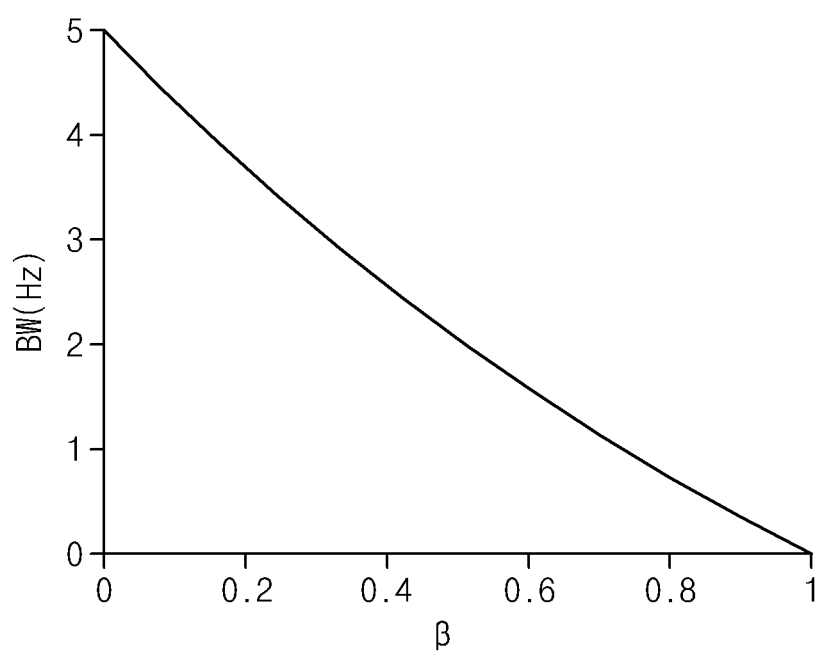
FIG. 2 is a view illustrating a relationship between a frequency band and a bandwidth-related parameter, according to an embodiment.

FIG. 2 is a description of a frequency tracking parameter according to an embodiment.

According to an embodiment, an electronic device (e.g., the electronic device 100 of FIG. 1) may obtain heart beat information based on frequency estimation. The electronic device may analyze the frequency of the obtained signal and may perform oscillator-based adaptive frequency tracking applying a time-varying bandpass filter together, and thus the electronic device may measure heart beat information without obtaining the peak interval from the pulse wave signal. The heart beat information may include HR and/or HRV.

According to an embodiment, an adaptive filter may be used upon performing heart beat monitoring based on frequency tracking. The adaptive filter may include a technology using adaptive line-enhancers (ALE) based on an infinite impulse response (IIR) filter, to effectively remove a noise in a measurement signal where an interest signal and the noise are mixed. The ALE may be implemented based on linear prediction that predicts a signal to be output later, by linearly combining a previous signal.

The features of adaptive filter-based frequency tracking may be determined by the following two parameters. The frequency tracking parameter may include a bandwidth-related parameter β and a forgetting factor δ. FIG. 2 illustrates a relationship between a band width-related parameter and a bandwidth. Referring to FIG. 2, when the bandwidth-related parameter is smaller, the bandwidth may be wider. In addition, in the adaptive band pass filter, when the forgetting factor is smaller, the influence on the previously-estimated value may be smaller.

The following Equations 1 to 4 are equations for obtaining parameters according to various embodiments disclosed in the specification.

Equation 1 represents an oscillator equation; Equation 2 represents a formula of an IIR filter; Equation 3 represents a bandwidth of a filter; Equation 4 represents a formula of an adaptive band pass filter.

Oscillator equation: $x(n) = 2\cos(\omega) \cdot x(n-1) - x(n-2)$ [Equation 1]

IIR Band-pass Filter: $H(z;n) = \frac{1-\beta}{2} \cdot \frac{1-z^{-2}}{1-\alpha(n)(1+\beta)z^{-1}+\beta z^{-2}}$ [Equation 2]

Bandwidth: $\cos^{-1}\left(\frac{2\beta}{1+\beta^2}\right)$ [Equation 3]

Adaptive Band-passFilter: $P(n) = \delta \cdot P(n-1) + (1-\delta) \cdot x^2(n-1)$ [Equation 4]

In Equation 1, 'w' may be a normalized instantaneous frequency value; 'n' may be the order of input signals. In Equation 2, β may be a bandwidth-related parameter; α(n) may be a correction function; 'z' may be an input signal. In Equation 4, δ may be a forgetting factor.

The frequency tracking parameter of a heart rate monitoring (HRM) algorithm may be changed to reflect a better HRV.

For example, when the two parameters are adjusted, the change in heart beat information may be tracked more rapidly, the equalization effect is reduced, and more variability may be reflected. Hereinafter, the configuration of an electronic device including a tracker operating as a band pass filter will be described.

Figure 3:
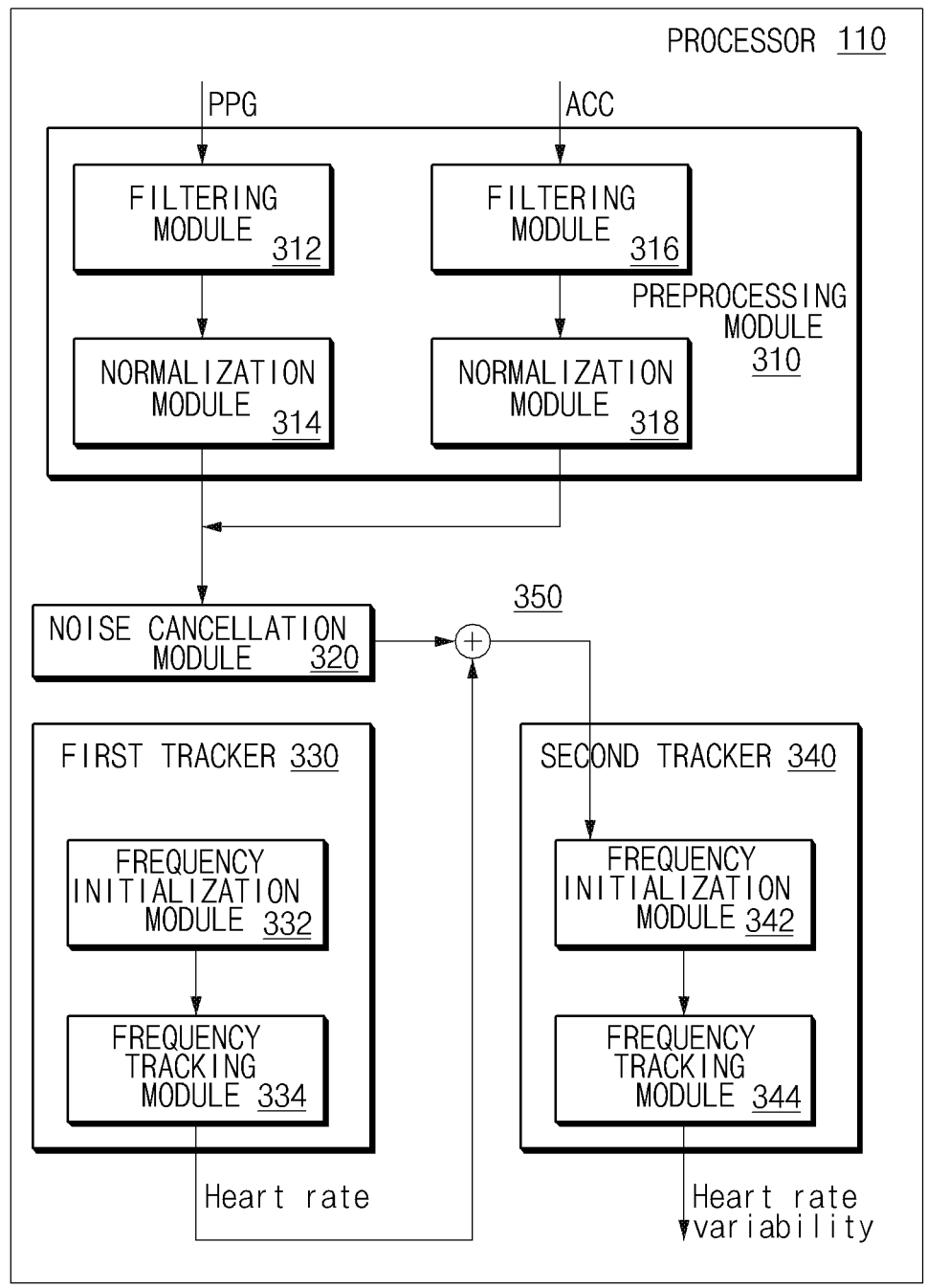
FIG. 3 is a block diagram illustrating a configuration a functional configuration of a processor according to an embodiment.

FIG. 3 is a block diagram illustrating a configuration a functional configuration of a processor according to an embodiment.

According to an embodiment, the processor 110 (e.g., the processor 110 in FIG. 1) may include a preprocessing module 310, a noise cancellation module 320, a first tracker 330, a second tracker 340, or a calculation module 350. In various embodiments, the processor 110 may omit a part of the above-mentioned components or may further include other components. In various embodiments, at least part of components included in the processor 110 of FIG. 3 may be implemented with software or hardware. For example, the operation of each of the modules may be stored in a memory in the form of an instruction and may be performed by the processor.

According to an embodiment, the preprocessing module 310 may perform preprocessing of the obtained signal. The preprocessing module 310 may filter and normalize the obtained signal. For example, the preprocessing module 310 may filter signals in a band, which may not be determined as a biometric signal, with respect to signals associated with an external object and then may normalize the magnitude distribution of the filtered signal. For example, the preprocessing module 310 may include at least one filtering module 312 or 316 and normalization module 314 or 318, which process each signal. The biometric signal (PPG) may be processed by the filtering module 312 and the normalization module 314; the motion signal (ACC) may be processed by the filtering module 316 and the normalization module 318.

According to an embodiment, the noise cancellation module 320 may remove a noise from the pre-processed signal associated with the external object. The noise cancellation module 320 may remove the noise caused by the motion of the electronic device 100 from the pre-processed biometric signal, using the pre-processed motion signal. According to an embodiment, the noise cancellation module 320 may perform noise cancellation signal processing, using an adaptive filter. An algorithm based on the steepest descent, least mean square (LMS), and recursive least square (RLS) methods may be used as an example of a scheme in which the noise cancellation module 320 collects a signal and then optimizes a filter coefficient of an adaptive filter to be suitable for the features of the signal. For example, the noise cancellation module 320 may include an adaptive noise cancellation module.

According to an embodiment, the first tracker 330 and the second tracker 340 may process the signal, from which the noise is removed and which is associated with the external object, and may calculate heart beat information. For example, the heart beat information may include HR, HRV, and/or derived other biometric information.

According to an embodiment, the first tracker 330 and the second tracker 340 may process the signal associated with the external object in the different signal processing schemes. According to an embodiment, the first tracker 330 and/or the second tracker 340 may use a frequency tracking method upon calculating the heart beat information. The first tracker 330 and/or the second tracker 340 may use the frequency tracking method, but may use different values with respect to at least some attributes used upon tracking the frequency. For example, the first tracker 330 and/or the second tracker 340 may be configured such that parameters for frequency tracking (hereinafter tracking parameters)

have different values. For example, herein, the tracking parameter may include forgetting factor δ and/or bandwidth-related parameter β. The parameters of the first tracker 330 and/or the second tracker 340 may be referred to as first tracking parameter and second tracking parameter, respectively.

According to an embodiment, the first tracker 330 may calculate first heart beat information based on a signal associated with an external object. The second tracker 340 may calculate second heart beat information based on a signal associated with an external object; alternatively, the second tracker 340 may obtain third heart beat information of a different type from a type of the second heart beat information, based on at least the second heart beat information; alternatively, the second tracker 340 may calculate connectivity between the first heart beat information and the second heart beat information. The processor 110 may obtain the second heart beat information, and/or connectivity through the second tracker 340. For example, the connectivity may be identified using a correlation coefficient or a trend feature. The first heart beat information and the second heart beat information may be the HR calculated by each of the trackers 330 and 340, or may be derived biometric information including the HR. The third heart beat information may be HRV, or may be the derived biometric information including the HRV.

According to an embodiment, the first tracker 330 may be configured to search for the main frequency of the heart beat band. The first tracker 330 may be used for dynamic noise cancellation and stable heart beat tracking.

According to an embodiment, the first tracker 330 may calculate first heart beat information based on a signal associated with an external object. The first tracker 330 may analyze the frequency of the biometric signal from which a noise is removed, and may track the frequency. The processor 110 may obtain the first heart beat information through the first tracker 330.

According to an embodiment, the first tracker 330 may have the attribute of a band pass filter. According to an embodiment, the first tracker 330 may filter the signal associated with the external object, but at least part of the tracking parameters of the first tracker 330 may be configured to have features of a relatively narrow-band pass filter. That is, the first tracker 330 may be referred to as a first filter. The first tracker 330 may filter the signal in the first frequency band, and the first frequency band may be set to be narrower than the second frequency band to be described later.

According to an embodiment, at least part of attributes of the first tracker 330 may be set to a first value. In other words, the tracking parameter of the first tracker 330 may be set to the first value. Hereinafter, the value of the tracking parameter applied to the first tracker 330 may be referred to as a first parameter value. The first parameter value and the center frequency of the first tracker 330 may have predetermined values. According to an embodiment, the first tracker 330 may obtain the first heart beat information, using the first parameter value.

According to an embodiment, the processor 110 may deliver the first heart beat information to the second tracker 340.

As compared to the first tracker 330, the second tracker 340 may be configured to have a large variation in frequency band and a small degree of signal equalization. In other words, the electronic device (e.g., the electronic device 100 of FIG. 1) may set the second tracker 340 such that the variability (hereinafter referred to as "heart rate variability" or "HRV") of the heart beat is reflected.

According to an embodiment, the second tracker 340 may analyze the frequency of the biometric signal from which a noise is removed, and may track the frequency. According to an embodiment, the second tracker 340 may process the signal associated with the external object in a signal processing method different from the signal processing method of the first tracker 330. The second tracker 340 may track the frequency while adjusting at least some attributes. To this end, the tracking parameter of the second tracker 340 may be set to have a second value.

According to an embodiment, the second tracker 340 may have an attribute of a band pass filter. According to an embodiment, the second tracker 340 may filter the signal associated with the external object, but at least part of the tracking parameters of the second tracker 340 may be configured to have features of a relatively wide-band pass filter. That is, the second tracker 340 may be referred to as a second filter. The second tracker 340 may filter the signal in the second frequency band, and the second frequency band may be set to be wider than the first frequency band.

According to an embodiment, at least part of attributes of the second tracker 340 may be set to the second value. The second tracker 340 may apply the second value different from the first value. Hereinafter, the value of the parameter applied to the second tracker 340 may be referred to as a second parameter value. According to an embodiment, the second parameter value may be set such that the second frequency band is wider than the first frequency band, and the equalization effect of the second tracker 340 is less than that of the first tracker 330. For example, a frequency band-related parameter and a forgetting factor value that are the second parameter value may be smaller than the first parameter value. The second parameter value may be varied. Details about the determination of the second parameter value will be described later.

According to an embodiment, the second tracker 340 may obtain second heart beat information, using the second parameter based on an input signal. The input signal of the second tracker 340 may be the biometric information obtained from the noise cancellation module 320, and/or the first heart beat information obtained from the first tracker 330.

According to an embodiment, the calculation module 350 may receive biometric information from which the noise is removed, and the first heart beat information obtained from the first tracker 330, and may perform calculation. The operation may be an arithmetic operation (e.g., a sum operation) or a comparison operation.

According to an embodiment, the processor 110 or the second tracker 340 may determine the second parameter value. The processor 110 may determine the second parameter value based on the first heart beat information, or may determine the second parameter value based on the connectivity (e.g., a correlation coefficient or a trend feature) between first heart beat information and second heart beat information. In addition, the processor 110 may determine the second parameter value based on various methods.

According to an embodiment, the processor 110 may determine heart rate variability (hereinafter referred to as HRV) based on at least one of the first heart beat information or the second heart beat information. According to an embodiment, the HRV may be determined by a second tracker or a separate module.

According to an embodiment, the first heart beat information may directly or indirectly affect the second heart beat information to determine the HRV. For example, the second heart beat information or second parameter may be determined based on the first heart beat information, and the HRV may be determined based on the second heart beat information. As a result, the first heart beat information may indirectly influence the determination of the HRV.

According to an embodiment, the processor 110 may compare the second heart beat information and the first heart beat information. The processor 110 may identify the connectivity between each other based on the first heart beat information and second heart beat information. According to an embodiment, the connectivity may be determined by a second tracker or a separate module. The processor 110 may determine the third heart beat information in response to the identifying of the connectivity.

According to an embodiment, frequency initialization modules 332 and 342 may set attributes of the trackers 330 and 340. For example, the frequency initialization modules 332 and 342 may set a frequency band-related parameter and/or a forgetting factor value.

According to an embodiment, frequency tracking modules 334 and 344 may track the frequency of a signal associated with biometric information measured in an external object, depending on the attributes determined by the frequency initialization modules 332 and 342.

Figure 4:
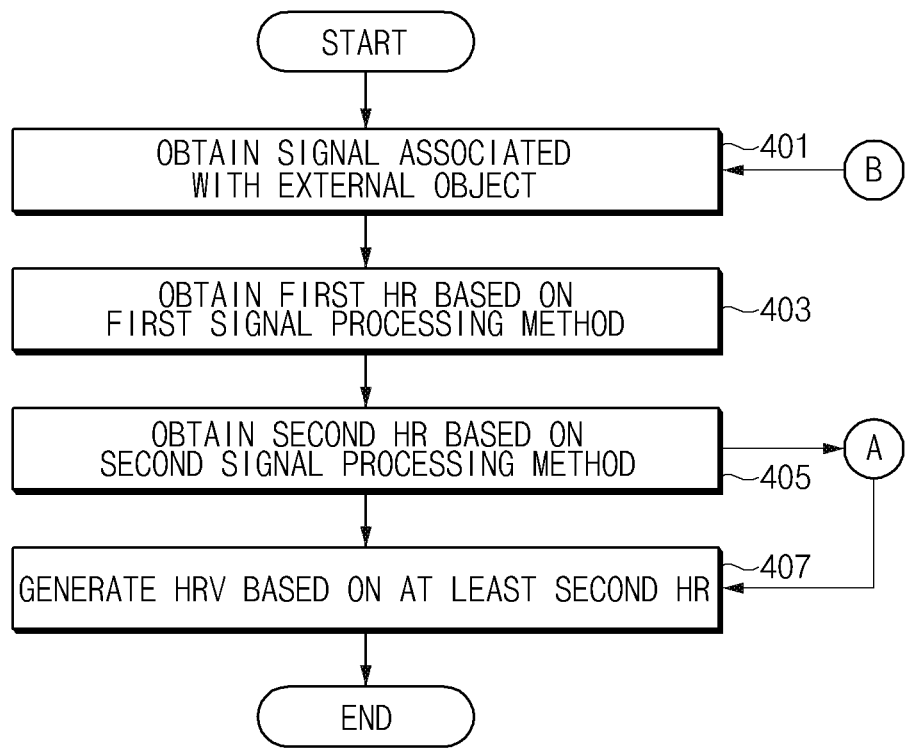
FIG. 4 illustrates a method, in which an electronic device obtains heart beat information, according to an embodiment.

FIG. 4 illustrates a method, in which an electronic device obtains heart beat information, according to an embodiment.

The operations illustrated in FIG. 4 may be performed by an electronic device (e.g., the electronic device 100 of FIG. 1). The operations are performed by a processor (e.g., the processor 110 of FIG. 1 or 3), and may be stored in a memory (e.g., the memory 120 of FIG. 1) in the form of an instruction.

In operation 401, the electronic device may obtain a signal associated with an external object. For example, the information associated with the external object may be a signal obtained by performing pre-processing on a signal obtained by a sensor (e.g., sensor 132 of FIG. 1) or by removing a noise from the signal obtained by the sensor. For example, the signal associated with the external object may be a biometric signal from which noise is removed.

In operation 403, the electronic device may obtain a first HR based on a first signal processing method. For example, the first signal processing method may be obtaining the first HR by using a first parameter value. Here, the first parameter value may be a fixed or preset value. The electronic device may calculate the first HR based on the signal associated with the external object by using the first parameter value.

In operation 405, the electronic device may obtain a second HR based on a second signal processing method. For example, the second signal processing method may be obtaining the second HR, using a second parameter value. The second parameter value may be a variable value. The electronic device may adaptively determine the second parameter value. The electronic device may obtain the second HR based on the signal associated with the external object, using the second parameter value.

In operation 407, the electronic device may generate an HRV based on at least the second HR.

Here, when the connectivity between the first HR and the second HR is reduced, the obtained HRV may be inaccurate. According to an embodiment, the electronic device may perform an operation of 'A' and operations after the operation of 'A' to determine a second parameter value for obtaining a more accurate HRV value. After operation 405, operations after the operation of 'A' may be further performed. The details may be described with reference to FIG. 5.

Figure 5:
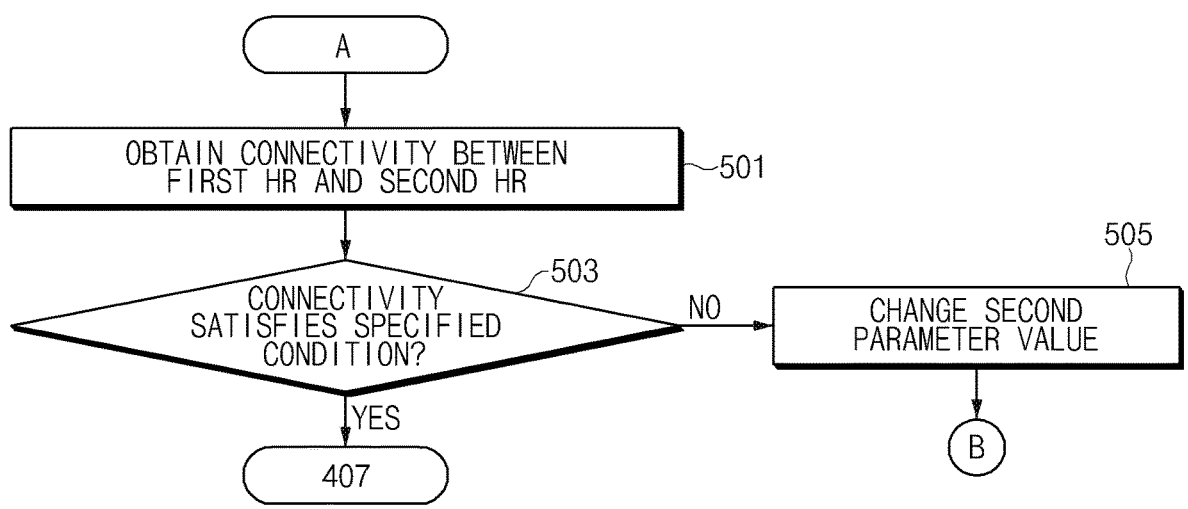
FIG. 5 is a flowchart of a method, in which an electronic device obtains an optimal parameter, according to an embodiment.

FIG. 5 illustrates a flowchart of a method, in which an electronic device obtains an optimal parameter, according to an embodiment.

The operations illustrated in FIG. 5 may be performed by an electronic device (e.g., the electronic device 100 of FIG. 1). The operations are performed by a processor (e.g., the processor 110 of FIG. 1 or 3), and may be stored in a memory (e.g., the memory 120 of FIG. 1) in the form of an instruction.

In operation 501, the electronic device may obtain connectivity between the HRs, using a first HR and a second HR. The connectivity may be identified based on a correlation coefficient or a trend feature.

In operation 503, the electronic device may determine whether the connectivity satisfies a specified condition. Operation 501 and operation 503 may be performed by a second tracker (e.g., the second tracker 340 of FIG. 3).

When the connectivity does not satisfy the specified condition (e.g., when the correlation coefficient is not greater than a threshold), in operation 505, the electronic device may change the second parameter value. Afterward, the electronic device may perform an operation of 'B' and operations after the operation of 'B', using the second parameter value.

When the connectivity satisfies the specified condition (e.g., when the correlation coefficient exceeds the threshold), the electronic device may determine the second parameter value used in operation 405 of FIG. 4 as an optimal second parameter value. Afterward, the electronic device may obtain the HRV in operation 407 of FIG. 4 based on the second HR obtained using the optimal second parameter value.

In FIG. 4, an operation after the operation of 'B' is performed as an operation after operation 401 in FIG. 4, but an operation after operation 405 in FIG. 4 may also be performed.

Figure 6:
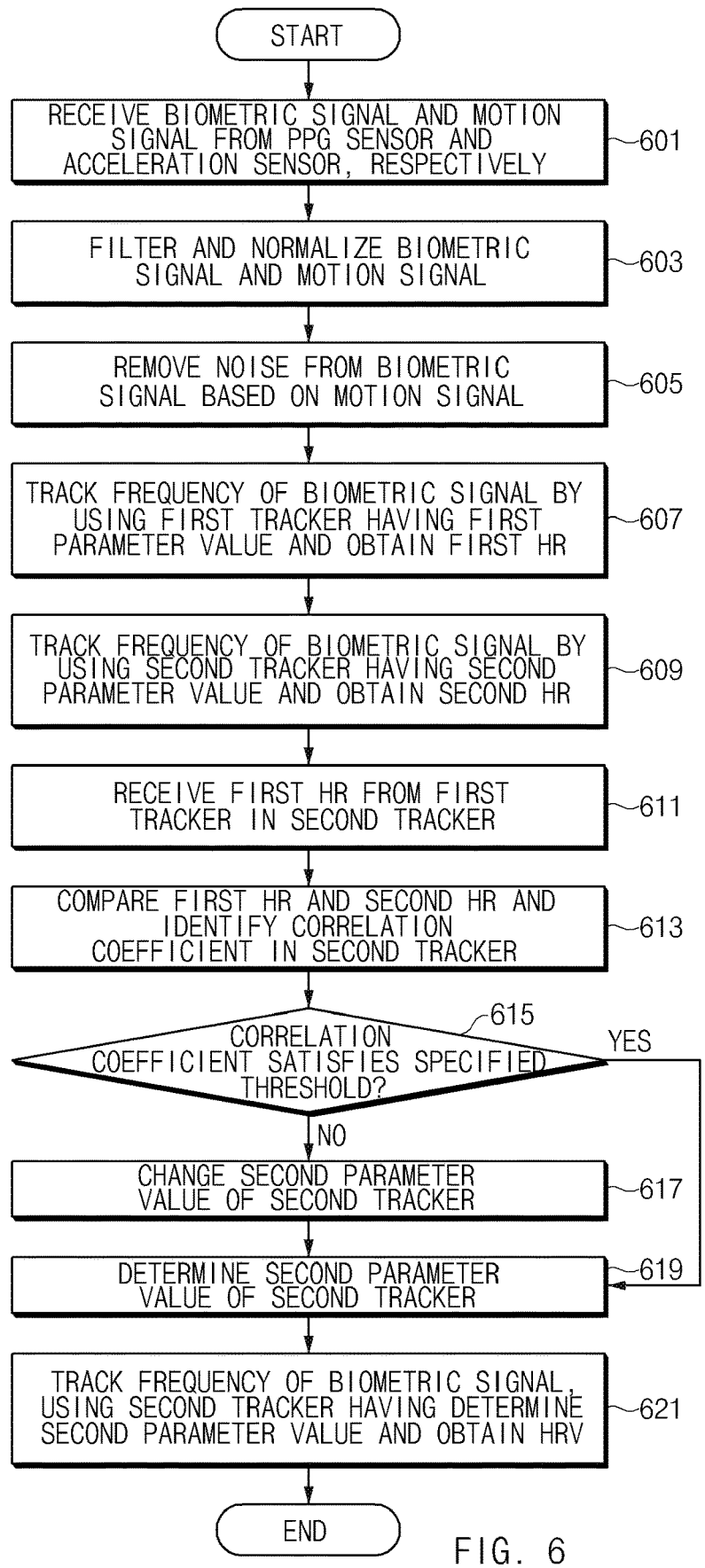
FIG. 6 is a flowchart of a method, in which an electronic device obtains a HRV, according to an embodiment.

FIG. 6 is a flowchart of a method, in which an electronic device obtains a HRV, according to an embodiment.

The operations illustrated in FIG. 6 may be performed by an electronic device (e.g., the electronic device 100 of FIG. 1). The operations are performed by a processor (e.g., the processor 110 of FIG. 1 or 3), and may be stored in a memory (e.g., the memory 120 of FIG. 1) in the form of an instruction. According to an embodiment, the electronic device may determine a second parameter value for obtaining a second HR, using a correlation coefficient of a first HR and the second HR, and may obtain the HRV. The correlation coefficient is a statistical meaning indicating a type of relationship; when the correlation coefficient is close to 1, the correlation coefficient may mean strong bond. Hereinafter, a method of determining the second parameter value based on the correlation coefficients between a first HR and a second HR and obtaining a HRV will be described.

In operation 601, the electronic device may obtain a signal associated with an external object through a sensor (e.g., the sensor 132 of FIG. 1) or a communication circuit (e.g., the communication circuit 140 of FIG. 1). The signal associated with the external object may include at least a biometric signal. For example, the electronic device may obtain the biometric signal from a PPG sensor and may obtain a motion signal from an acceleration sensor. For example, the electronic device may obtain the biometric signal or motion signal from an external electronic device through the communication circuit.

In operation 603, the electronic device may filter and normalize the signal associated with the external object. For example, the electronic device may filter and normalize the biometric signal and the motion signal. The electronic device may filter each signal to remove signals in unnecessary bands from the biometric signal and the motion signal. The electronic device may normalize each of the filtered signals.

In operation 605, the electronic device may remove a noise from a signal (or a biometric signal) associated with the external object. The electronic device may remove the noise in the biometric signal, based on the motion signal. Here, noise cancellation may be performed on the filtered and normalized biometric signal.

In operation 607, the electronic device may track the frequency of the biometric signal and may obtain the first HR. The electronic device may track the frequency of the biometric signal, using the first parameter value. For example, the electronic device may track the frequency of the biometric signal, using the first tracker (e.g., the first tracker 330 of FIG. 3) and may obtain the first HR. The parameter corresponding to the first parameter value may be two parameters. For example, the parameter may include a bandwidth-related parameter and a forgetting factor. For example, the bandwidth-related parameter for the first tracker may be 0.98, and the forgetting factor may be 0.97.

In operation 609, the electronic device may track the frequency of the biometric signal and may obtain the second HR. The electronic device may track the frequency of the biometric signal, using the second parameter value. For example, the electronic device may track the frequency of the biometric signal, using the second tracker (e.g., the second tracker 340 of FIG. 3) and may obtain the second HR. At least one of the bandwidth-related parameter or the forgetting factor included in the second parameter value may be a value different from the first parameter value. For example, the bandwidth-related parameter among the second parameter values may be smaller than the first parameter value. As a result, the bandwidth of the second tracker may be set to be greater than the bandwidth of the first tracker. The forgetting factor among the second parameter value may be smaller than the first parameter value.

In operation 611, the second tracker may obtain the first HR. The second tracker may receive the first HR from the first tracker.

In operation 613, the electronic device may identify the connectivity between the first HR and the second HR. For example, the electronic device may compare the first HR and the second HR and may identify a correlation coefficient. The second tracker may calculate the correlation coefficient, using the first HR and the second HR.

In operation 615, the electronic device may determine whether the correlation coefficient satisfies a specified threshold. According to an embodiment, the electronic device may determine whether the correlation coefficient satisfies the specified threshold. For example, the electronic device may determine whether the correlation coefficient is greater than a threshold. This operation may be performed by the second tracker. The threshold may be an experimentally-determined value based on statistics or learning.

When the correlation coefficient satisfies the specified threshold (or when the correlation coefficient is greater than the specified threshold), the electronic device may perform operation 619. The electronic device may determine the second parameter value used in operation 609, as an optimal second parameter value. In operation 621, the electronic device may track the frequency of the biometric signal continuously received using the optimal second parameter value. Afterward, the electronic device may obtain the HRV, using a second tracker having the second parameter value.

When the correlation coefficient does not satisfy the threshold (or when the correlation coefficient is less than or equal to the threshold), the electronic device may change the second parameter value of the second tracker. The electronic device may repeatedly perform at least part of operation 601 to operation 613 on the second parameter value.

For example, after changing the second parameter value, the electronic device may obtain a sensing signal, may filter and normalize the sensing signal; after removing the noise of the biometric signal, the electronic device may obtain the second HR, using the first HR and the changed second parameter value. The electronic device may obtain the first HR and the second HR, may obtain a correlation coefficient, and may determine whether the correlation coefficient satisfies the specified threshold. It may be determined that the second parameter value for the case where the correlation coefficient satisfies the specified threshold is a second parameter value suitable to calculate the HRV. After determining the second parameter value, the electronic device may obtain the HRV, using the second tracker having the second parameter value.

Various changes of a sequence or an operation are possible in the embodiments disclosed in the specification. For example, operation 611 may be performed before operation 609 is performed and after operation 607 is performed. For another example, after performing operation 611, the electronic device may calculate the HRV using the first HR and the second HR; however, when the optimal second parameter value is determined, the corresponding HRV may be determined as an optimal HRV value. In this case, HRV information determined as the optimal HRV may be displayed on a display.

Figure 7:
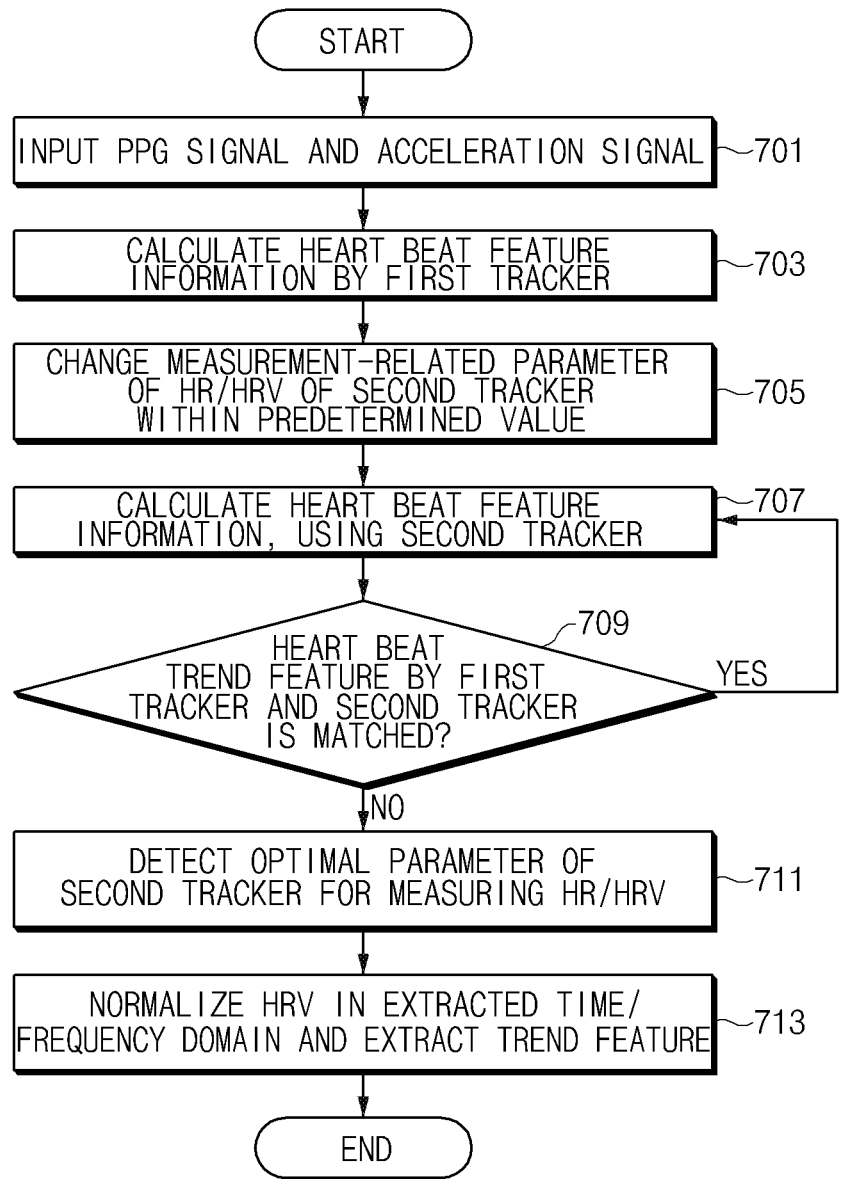
FIG. 7 is a flowchart of a method, in which an electronic device obtains a HRV, according to an embodiment.

FIG. 7 is a flowchart of a method, in which an electronic device obtains a HRV, according to an embodiment.

The operations illustrated in FIG. 7 may be performed by an electronic device (e.g., the electronic device 100 of FIG. 1). The operations are performed by a processor (e.g., the processor 110 of FIG. 1 or 3), and may be stored in a memory (e.g., the memory 120 of FIG. 1) in the form of an instruction. According to an embodiment, the electronic device may determine connectivity by identifying a heart beat tendency feature. The electronic device may determine the second parameter value using the heart beat tendency feature, and may obtain the HRV. According to an embodiment, the electronic device may obtain a trend feature based on heart beat feature information. For example, the heart beat feature information may be the heart beat information (e.g., HR).

In operation 701, the electronic device may obtain a signal associated with an external object. For example, the electronic device may obtain the biometric signal from a PPG sensor and may obtain a motion signal from an acceleration sensor. The motion signal may be an acceleration signal. For example, the electronic device may obtain the biometric signal or motion signal from an external electronic device through the communication circuit. The electronic device may input the signal associated with the external object to a first tracker (e.g., the first tracker 330 in FIG. 3) and/or a second tracker (e.g., the second tracker 340 in FIG. 3). Here, the signal associated with the external object input to the tracker may be a signal on which operation 601 to operation 605 of FIG. 6 are performed and from which a noise is removed. In addition, the input to a tracker or using the tracker may mean using a specific attribute value (or a parameter value) or using a specific signal processing method.

According to an embodiment, the electronic device may calculate the heart beat feature information using a first parameter value and a second parameter.

In operation 703, the electronic device may calculate first heart beat feature information by the first tracker. The electronic device may obtain the heart beat feature information from the biometric signal based on the first parameter value.

In operation 705, the electronic device may change a parameter value within a specific range. The specific range may be a predetermined value. The electronic device may change a measurement-related parameter of HR and/or HRV of the second tracker. The measurement-related parameter may be the tracking parameter of FIGS. 3 to 6. The corresponding parameter value may be the second parameter value.

In operation 707, the electronic device may calculate the heart beat feature information based on the second parameter value from the biometric signal. In other words, the electronic device may calculate second heart beat feature information by means of the second tracker.

In operation 709, the electronic device may determine whether a heart beat trend feature by means of the first tracker and the second tracker is matched. The electronic device may determine whether the heart beat trend feature is matched using the first heart beat feature information and the second heart beat feature information. The heart beat feature information and the heart beat trend feature will be described later.

When the heart beat trend feature is matched, the electronic device may perform operation 707.

When the heart beat trend feature is not matched, in operation 711, the electronic device may detect the optimal parameter. For example, the electronic device may detect an optimal parameter for measuring the HR and/or HRV. For example, the electronic device may determine the second parameter value used in operation 707, as the optimal second parameter value.

In operation 713, the electronic device may normalize the HRV in the extracted time/frequency domain and may extract a trend feature.

Again, in operation 709, the electronic device may analyze a heart beat trend feature, to determine whether the heart beat feature by means of the second tracker is reliable.

According to an embodiment, the electronic device (e.g., the electronic device 100 of FIG. 1) may identify the correlation between variables obtained from two trackers, using correlation analysis between the first heart beat feature information and the second heart beat feature information. The electronic device may make dispersion for finding the complete relationship between variables by plotting each of the variables on two axes in a graph or chart; when a perfect relationship is established, the electronic device may draw a straight line passing through all points.

According to an embodiment, the electronic device may also apply a phase synchronization and directionality analyzing method. It is impossible to infer the direction of influence between the two variables in the correlation analysis, and thus the above-described method may be effective.

The phase synchronization may be quantified in several manners. For example, the phase synchronization method includes a method of quantifying through synchrogram and recurrence plot for investigating a synchronization frequencies ratio between variables, and a method using entropy-based phase synchronization indicators ($\rho$, $\lambda$, $\gamma$).

According to an embodiment, the electronic device may extract the phase of each heart beat feature variable through a Hilbert transform and may set each cycle to investigate or quantify a synchronous feature transformation according to the ratio, and thus to display the investigated or quantified result as a graph.

According to an embodiment, the electronic device may analyze the influence caused by the heart beat variables measured by two trackers, through the phase synchronization analysis and the directionality analysis, as the magnitude of the directionality. The directionality analysis may be performed through a Granger causality index, partial directed coherence (PDC), and/or directionality index.

According to an embodiment, the electronic device may identify the heart beat trend feature, using the correlation analysis and/or phase synchronization analysis and directionality analysis described above. When determining, based on the trend feature, that the reliability of HRV information measured by the second tracker is capable of being secured, the electronic device may gradually adjust a parameter of the second tracker and may allow the optimal parameter to be calculated. For example, the electronic device may adjust the parameter while applying "%" to the parameter or numerically applying "+/−" to the parameter.

Figure 8:
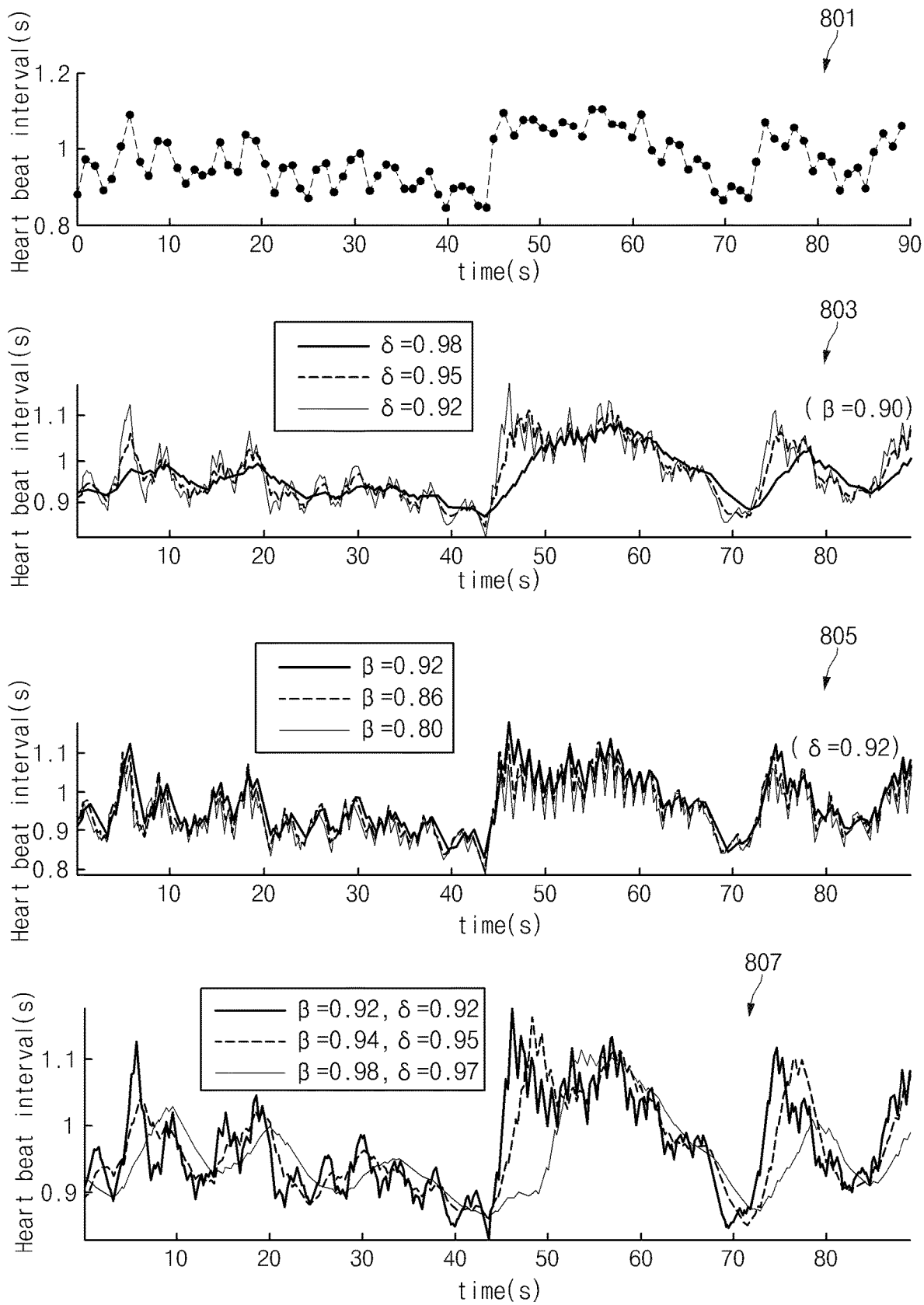
FIG. 8 is a graph illustrating a change in HRV according to a change in a parameter of a tracker, according to an embodiment.

FIG. 8 is a graph illustrating reflection of variability of heart beat information according to an embodiment.

A graph 1 801 represents "R to R interval" (RRI) as a reference heart beat interval measured by electrocardiography (ECG); graphs 2 to 4 803, 805, and 807 represent peak to peak interval (PPIs) as heart beat intervals estimated while tracking parameters ($\delta$, $\beta$) in the second tracker (e.g., the second tracker 340 in FIG. 3) are changed.

Here, it is assumed that the combination of tracking parameters ($\delta$, $\beta$) in the first tracker (e.g., the first tracker 330 in FIG. 3) (or the combination of first parameter values) is, for example, (0.97, 0.98). To calculate stable heart beat information in the corresponding simulation, the tracking parameters ($\delta$, $\beta$) of the first tracker have been set such that the band of frequency tracking is narrow and the degree of equalization is increased.

The graph 2 803 illustrates a feature that heart beat information tracking is changed while a forgetting factor $\delta$ is adjusted in oscillator frequency tracking (e.g., $\delta$=0.92, 0.95, or 0.98), through a simulation. The graph 2 803 is the result for a case where the bandwidth-related parameter $\beta$ is 0.90.

The graph 3 805 illustrates a feature that the heart beat information tracking is changed while a bandwidth-related parameter is adjusted in oscillator frequency tracking ($\beta$=0.80, 0.86, or 0.92), through a simulation. The graph 3 805 illustrates a case where the forgetting factor $\delta$ is 0.92.

The graph 4 807 illustrates a feature that heart beat information tracking is changed while the combination (or the combination of second parameter values) of tracking parameters ($\delta$, $\beta$) in the second tracker is changed differently, through a simulation.

Referring to the graph 2 803, it may be seen that the variability of the heart beat is greater as the forgetting factor is smaller. Referring to the graph 3 805, it may be seen that the variability of the heart beat is greater as the bandwidth-related parameter is smaller. Referring to the graph 4 807, it may be seen that the variability of the heart beat is greater when the bandwidth-related parameters $\beta$ and the forgetting factor $\delta$ are smaller.

Referring to FIG. 8, it may be seen that the variability of heart beat information is reflected by adjusting a bandwidth-related parameter and/or forgetting factor, which is a parameter associated with the frequency tracking variability of a tracker. As the forgetting factor is smaller or as the bandwidth-related parameter is smaller, the variability of heart beat information may be better reflected. On the other hand, as the forgetting factor is greater or as the bandwidth-related parameter is greater, the stable heart beat information may be obtained.

Figure 9:
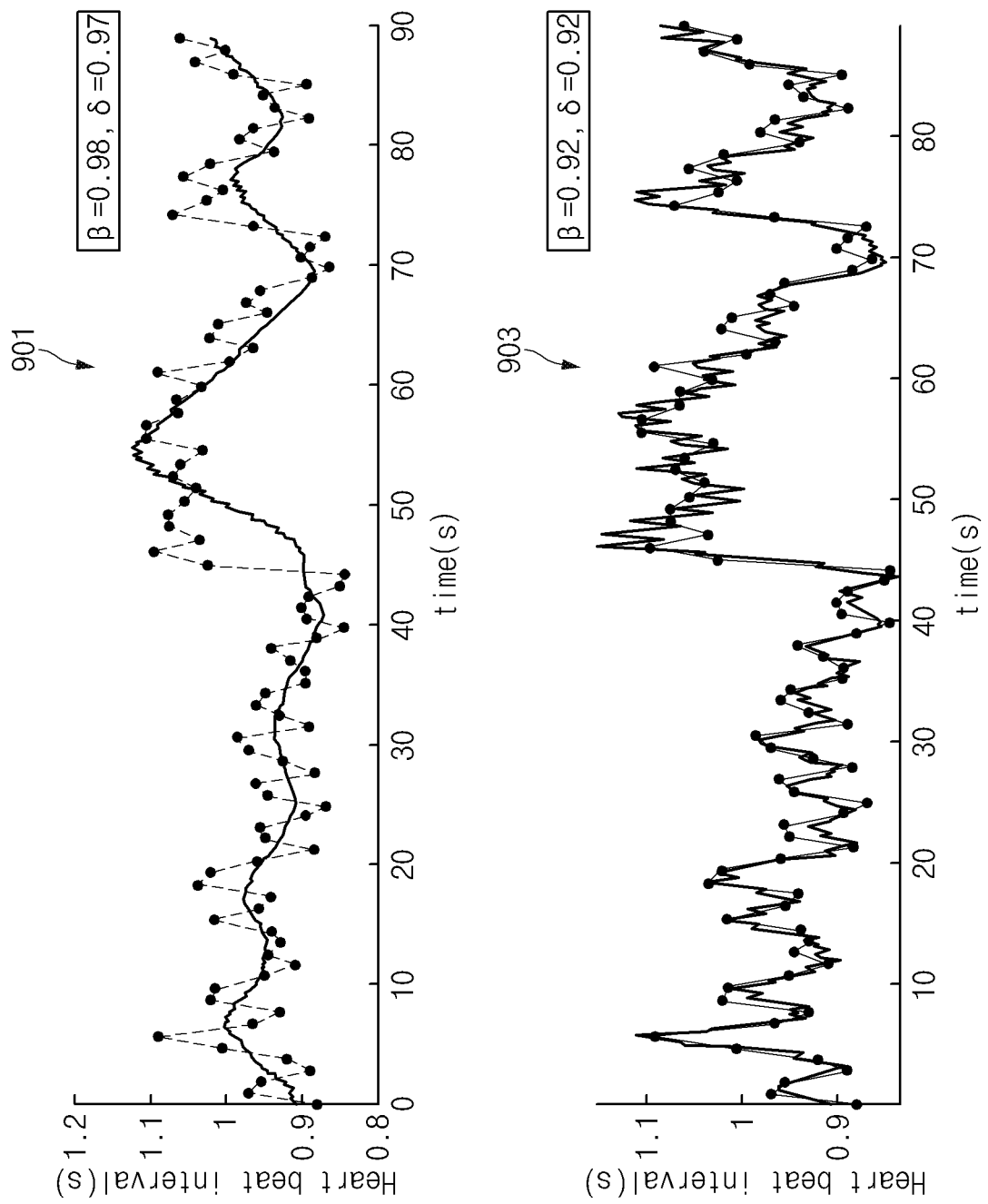
FIG. 9 illustrates a relationship between heart beat information and a combination of a parameter value of each of a first tracker and a second tracker, according to various embodiments.

FIG. 9 illustrates a relationship between heart beat information and a combination of a parameter value of each of a first tracker and a second tracker, according to various embodiments.

A graph 1 901 and a graph 2 903 are graphs illustrating the measured reference heart beat interval (dashed line) and the heart beat information frequency tracking result (solid line) at the same time. The graph 1 901 and the graph 2 903 illustrate the result for the combination of different tracking parameters (δ, β). For example, the graph 1 901 illustrates a case where the tracking parameter is (0.98, 0.97); for example, the graph 2 903 illustrates a case where the tracking parameter is (0.92, 0.92).

The graph 1 901 illustrates the tracking result when the bandwidth-related parameter and forgetting factor are larger than graph 2 903; the graph 1 901 illustrates a feature of the first tracker (e.g., the first tracker 330 in FIG. 3) used when the stability of heart beat information tracking is pursued.

The graph 2 903 illustrates a feature of the second tracker (e.g., the second tracker 340 in FIG. 3) focused on obtaining HRV variability when the relatively bandwidth-related parameter and the forgetting factor are small.

Referring to FIG. 9, it is possible to analyze a reliable section in which the trend feature of the heart beat feature information measured in the first tracker is maintained, through correlation analysis, phase synchronization and directionality analysis and to identify the variability using the second tracker within the section. To this end, an electronic device (e.g., the electronic device 100 of FIG. 1) may estimate a PPI value similar to an ECG-based heart beat interval by adjusting a tracking parameter in the method of setting a band to be wide and reducing dependence on the previous value to reduce equalization.

HRV analysis is mainly performed on the time and frequency range. HRV analysis in the time range is based on statistical information such as the average and standard deviation of the heart beat; information about the stability of the cardiovascular system, the control ability of the autonomic nervous system, and the activity of the parasympathetic nerve may be seen through parameters such as standard deviation of the NN interval (SDNN) and root mean square of the successive difference (RMSSD). Moreover, HRV analysis in the frequency range is performed on the range of low frequency, high frequency, or the like, which is divided based on a specific frequency (0.04, 0.15, or 0.4 Hz); the HRV analysis may provide information capable of evaluating the activity of the sympathetic and parasympathetic nerves or the overall autonomic nervous system.

Figure 10:
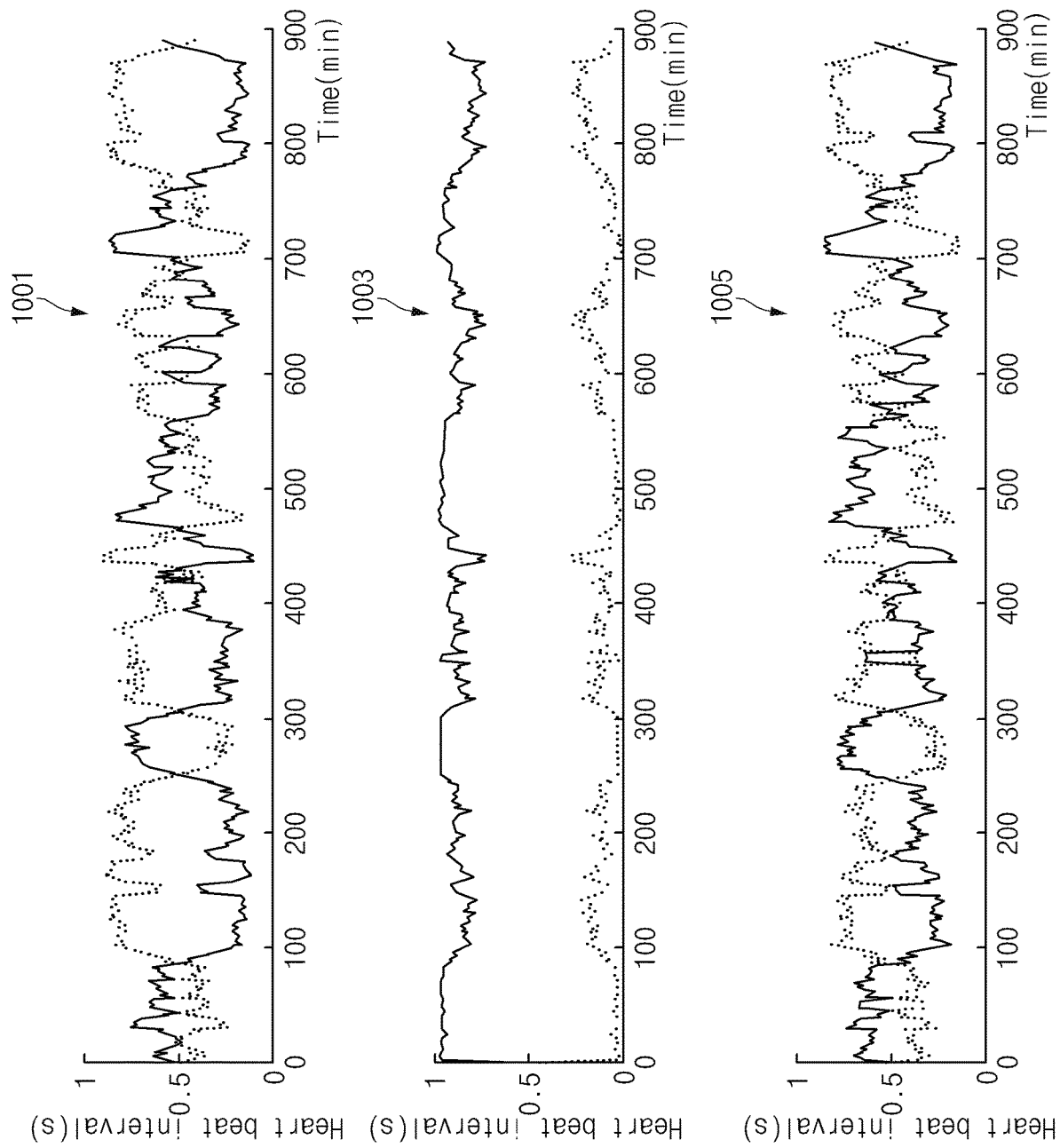
FIG. 10 illustrates a result of calculating a HRV value in a frequency domain using parameter optimization according to an embodiment.

FIG. 10 illustrates a result of calculating a HRV parameter in a frequency domain using parameter optimization according to an embodiment.

FIG. 10 is illustrated by obtaining HRV parameters (normalized low frequency (nLF) and normalized high frequency (nHF)) in the frequency domain after HRV variability appears in heart beat information estimated through PPG frequency tracking as illustrated in FIG. 9 using parameter optimization. In FIG. 10, the solid line represents nLF; the dotted line represents nHF.

A graph 1 1001 illustrates nLF and nHF obtained using the RRI of ECG measured as a reference; a graph 2 1003 illustrates nLF and nHF obtained using the PPI of the first tracker. A graph 3 1005 illustrates nLF and nHF obtained using the PPI of the second tracker.

Referring to the graph 2 1003, nLF and nHF of the first tracker appear to have low correlation with the reference of the graph 1 1001. Referring to the graph 3 1005, nLF and nHF of the second tracker appear to have high correlated with the reference of the graph 1 1001.

Referring to FIG. 10, it may be seen that the variability of HR is not well reflected in the first tracker because the tracking parameter reflecting low variability is set; on the other hand, it may be seen that the variability of HR is well reflected in the second tracker.

According to an embodiment, when frequency tracking-based HR extraction is made at equal intervals depending on the sampling rate of the electronic device, it is possible to increase the accuracy of HRV parameter estimation in a method of reconstruction PPI at nonequal intervals depending on a heart beat interval to obtain HRV parameters in a time domain.

Figure 11:
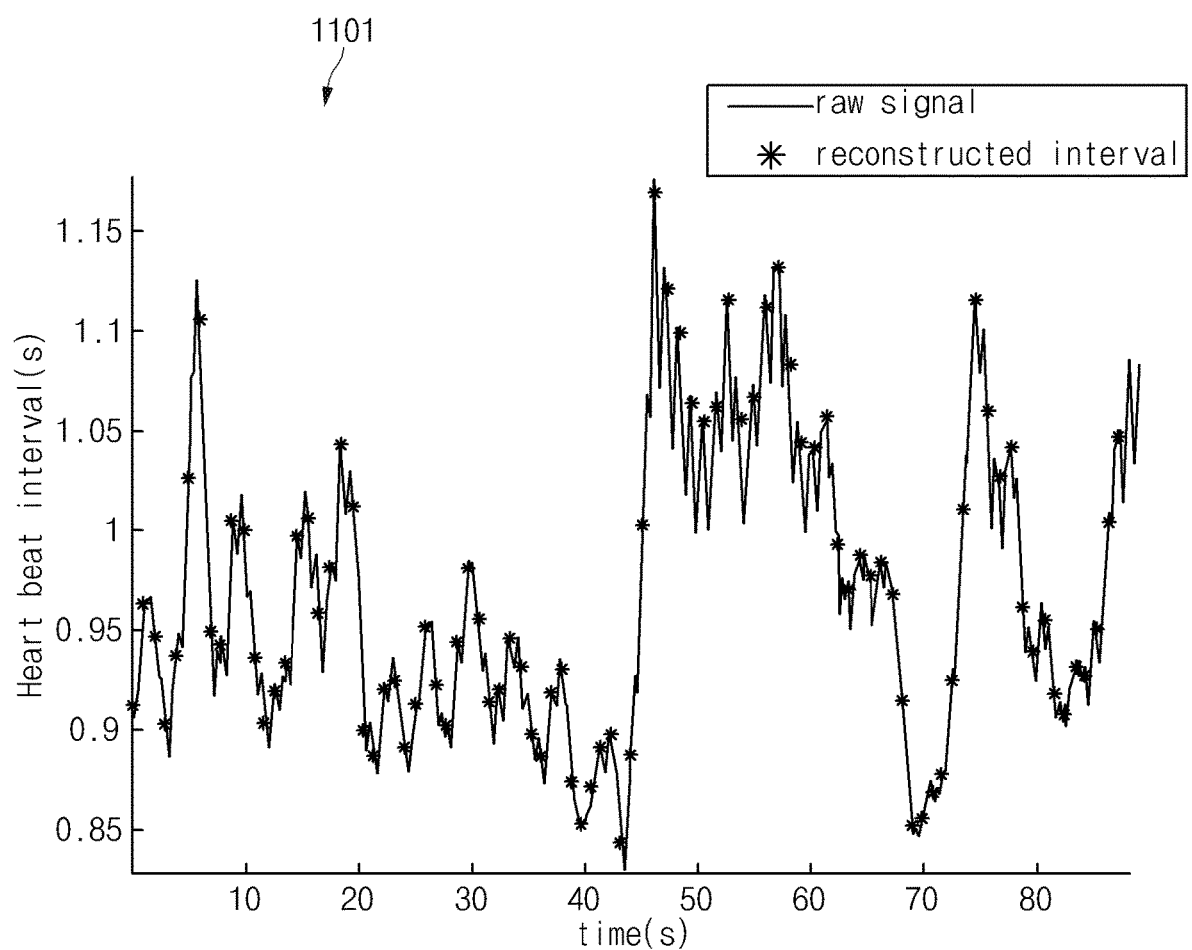
FIG. 11 is a diagram for presenting a description of a PPI reconstructing method.

FIG. 11 is a diagram for presenting a description of a PPI reconstructing method.

A graph 1101 illustrates raw data of a heart beat interval and sampling '*' for the corresponding data. As illustrated in the graph 1101, the PPI method may be a method of sampling a heart beat interval at a nonequal interval. For example, an electronic device (e.g., the electronic device 100 of FIG. 1) may repeat an operation of obtaining a current heart beat interval and determining that a sample, which is present after a time corresponding to a heart beat interval value, or a time corresponding to an interval value, is a next heart beat interval value. When the heart beat interval value is small, the time interval with the next sample value may be small; when the heart beat interval value is great, the time interval with the next sample value may be great.

Figure 12:
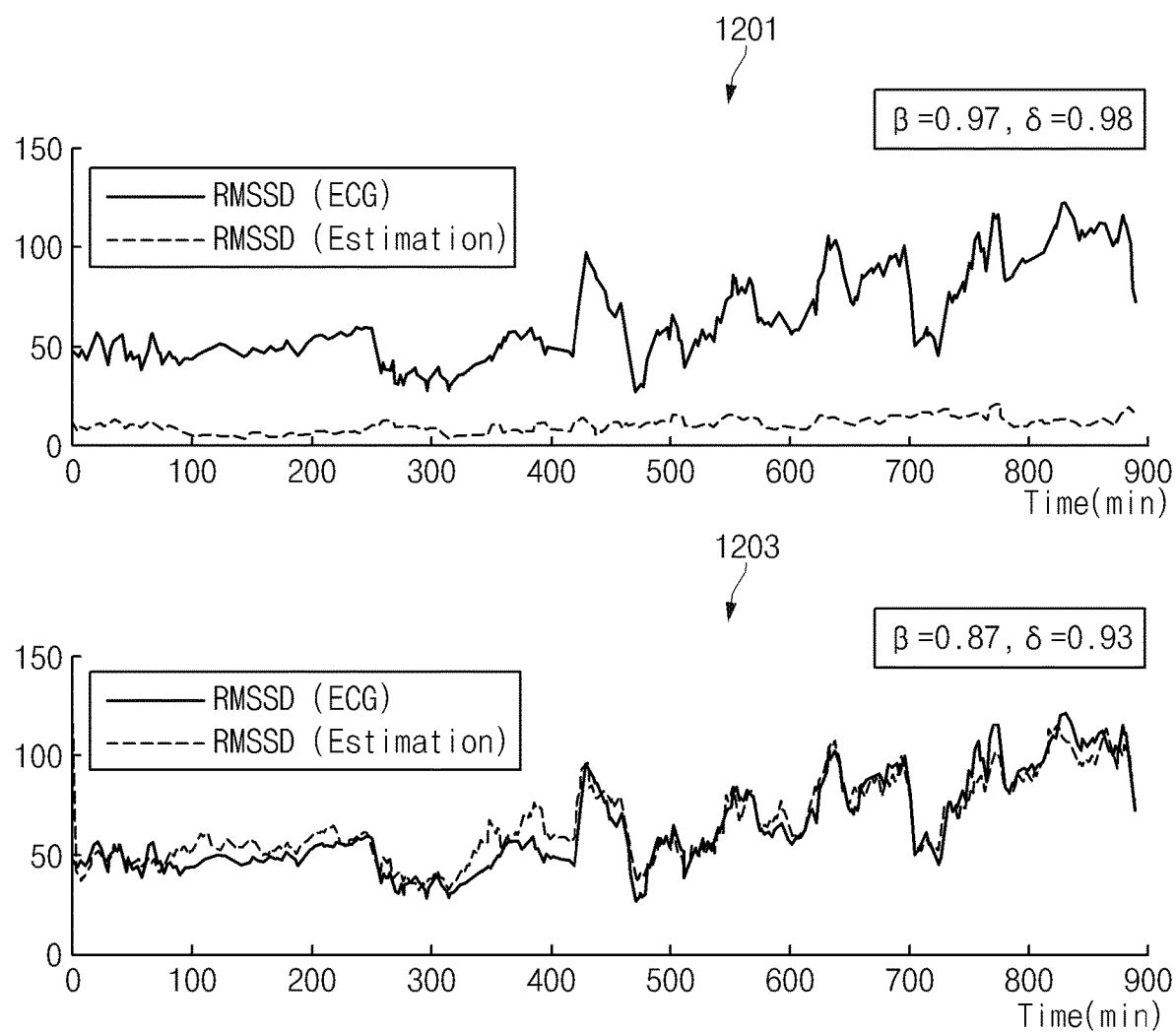
FIG. 12 illustrates an HRV value (RMSSD) in a time domain according to an embodiment.
Figure 13:
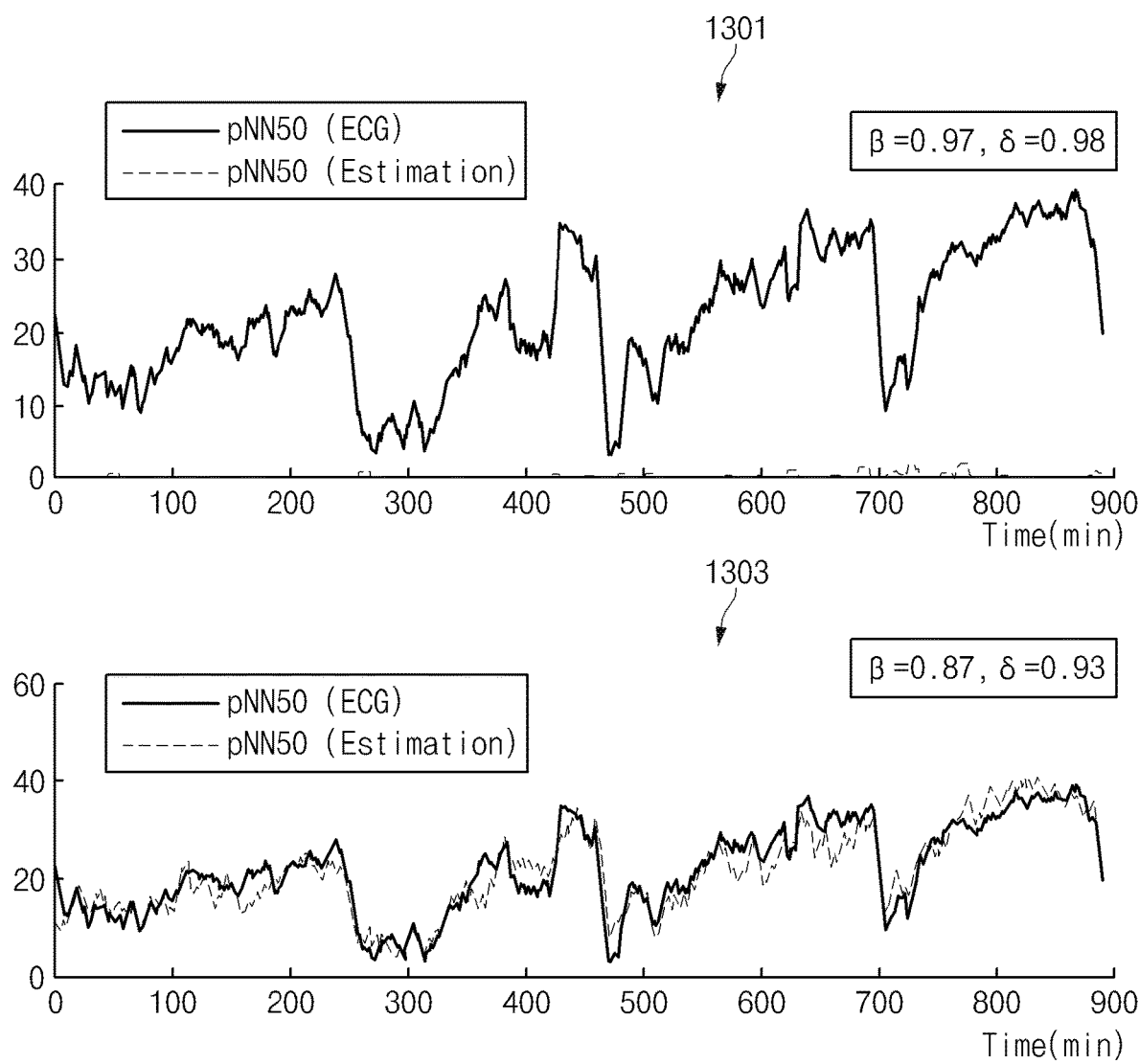
FIG. 13 illustrates an HRV value (pNN50) in a time domain according to an embodiment.

FIGS. 12 and 13 illustrate HRV parameter values calculated in a time domain according to an embodiment.

According to an embodiment, the HRV may be RMSSD or pNN50 (the proportion of "the number of pairs of successive NNs that differ by more than 50 ms (NN50))" divided by total number of NNs). In addition, HRV may also be measured in a variety of ways.

FIG. 12 illustrates HRV as RMSSD; a graph 1 1201 indicates a case where tracking parameters (δ, β) are, for example, (0.98, 0.97); a graph 2 1203 indicates a case where the tracking parameters are, for example, (0.93, 0.87).

FIG. 13 illustrates HRV as pNN50, and illustrates the result of calculating pNN50 according to tracking parameter combinations (δ, β). For example, the graph 1 1401 illustrates a case where the tracking parameter is (0.98, 0.97); for example, the graph 2 1403 illustrates a case where the tracking parameter is (0.93, 0.87).

In FIGS. 12 and 13, the solid line indicates the HRV measurement value calculated from ECG-based reference heart beat information; the dotted line indicates the HRV result value using heart beat information estimated using frequency tracking.

In other words, for example, (0.98, 0.97) is a parameter combination (first parameter value) of the first tracker; graphs 1 1201 and 1301 may be relatively stable HRV calculation values of the first tracker.

For example, (0.93, 0.87) may be a parameter combination (a second parameter value) of the second tracker; graphs 2 1203 and 1303 may be HRV calculation values of the second tracker focused on obtaining variability.

Referring to FIGS. 12 and 13, it is difficult to accurately estimate the HRV index in a time domain in the case where only the first tracker is used. However, when the HRV in the time domain is estimated using the second tracker to which nonequal interval sampling is applied, the electronic device (e.g., the electronic device 100 of FIG. 1) may accurately estimate the variability of the heartbeat through the second tracker while stably operating based on the first tracker.

According to an embodiment, the electronic device may determine the optimal parameter value of the second tracker, and may obtain an accurate HRV value, using the second tracker to which the optimal parameter is applied. The electronic device may perform sleep stage prediction and stress index measurement based on the HRV value obtained through the second tracker. Hereinafter, sleep stage prediction will be described.

Rapid eye movement (REM) sleep refers to a state of sleep that makes it possible to have a dream with light sleep. During REM sleep, a body is asleep but a brain is awake and active; accordingly, irregular biorhythms may appear and sympathetic nerves may be activated. At this time, in the cardiovascular system, HR and HRV may increase and may be irregular.

According to an embodiment, the electronic device may calculate a REM feature based on information about HR and HRV.

Figure 14:
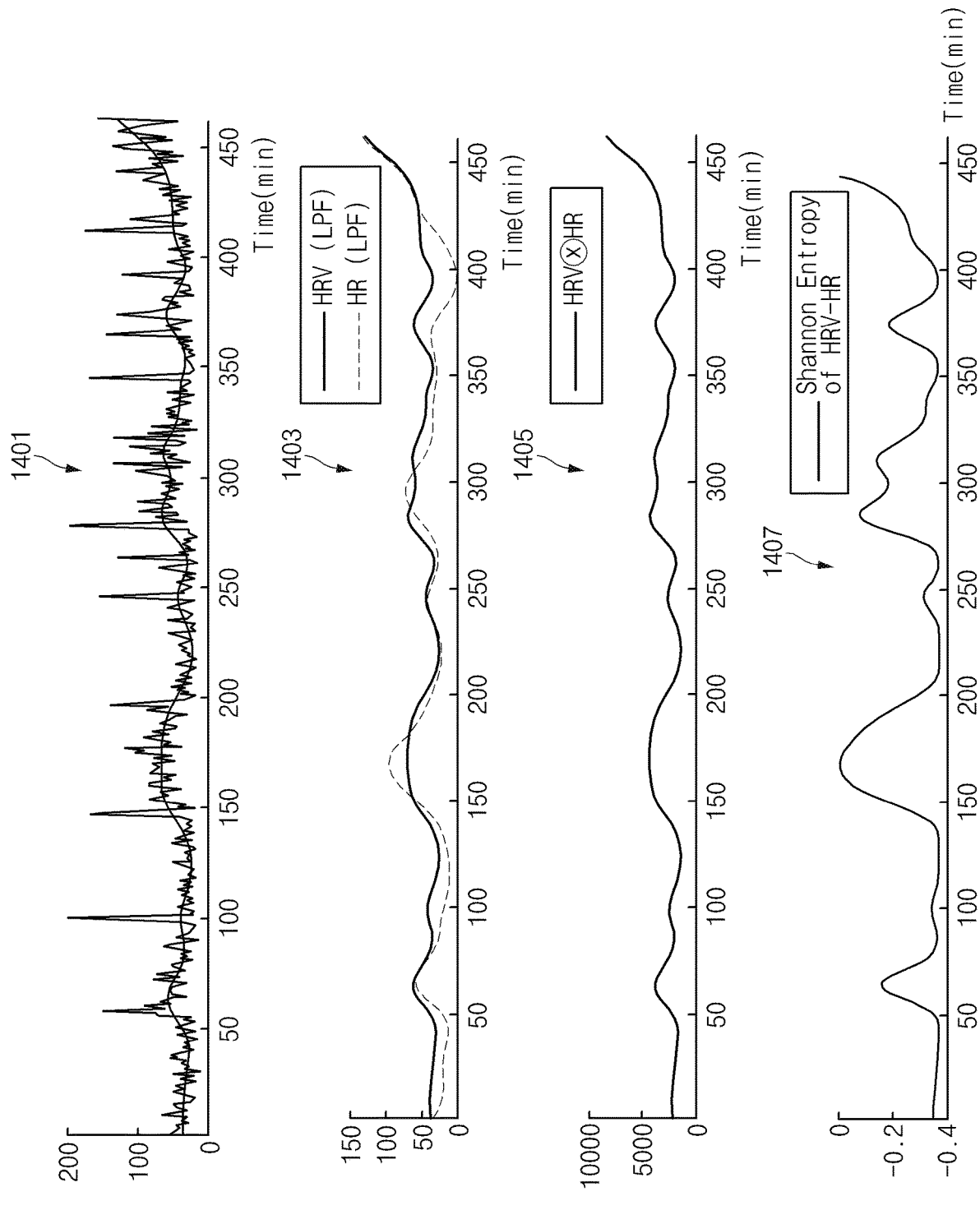
FIG. 14 is a graph of estimating a sleep pattern according to an embodiment.

FIG. 14 is a graph for calculating REM features according to an embodiment.

A graph 1 11401 is a graph illustrating raw data of HR and HRV.

A graph 2 1403 is a graph from extracting a low frequency pattern of data by applying a low band pass filter. Because the cycle of sleep leading to wake, light sleep, deep sleep, and REM sleep usually has a period of about 1.5 to 2 hours, an electronic device (e.g., the electronic device 100 of FIG. 1) may extract a low frequency pattern by applying a low pass filter to HR and HRV such that the period of the sleep cycle is reflected. In the graph 2 1403, the solid line indicates HRV according to sleep, and the dotted line indicates HR.

A graph 3 1405 illustrates the REM feature of an intermediate stage generated by combining HR and HRV. The REM feature of an intermediate stage may be represented through the various operations on the HR and HRV.

A graph 4 1407 illustrates Shannon-entropy of the value obtained by combining HR and HRV. The electronic device may apply Shannon-entropy signal processing, in a method of emphasizing a main peak component.

Figure 15:
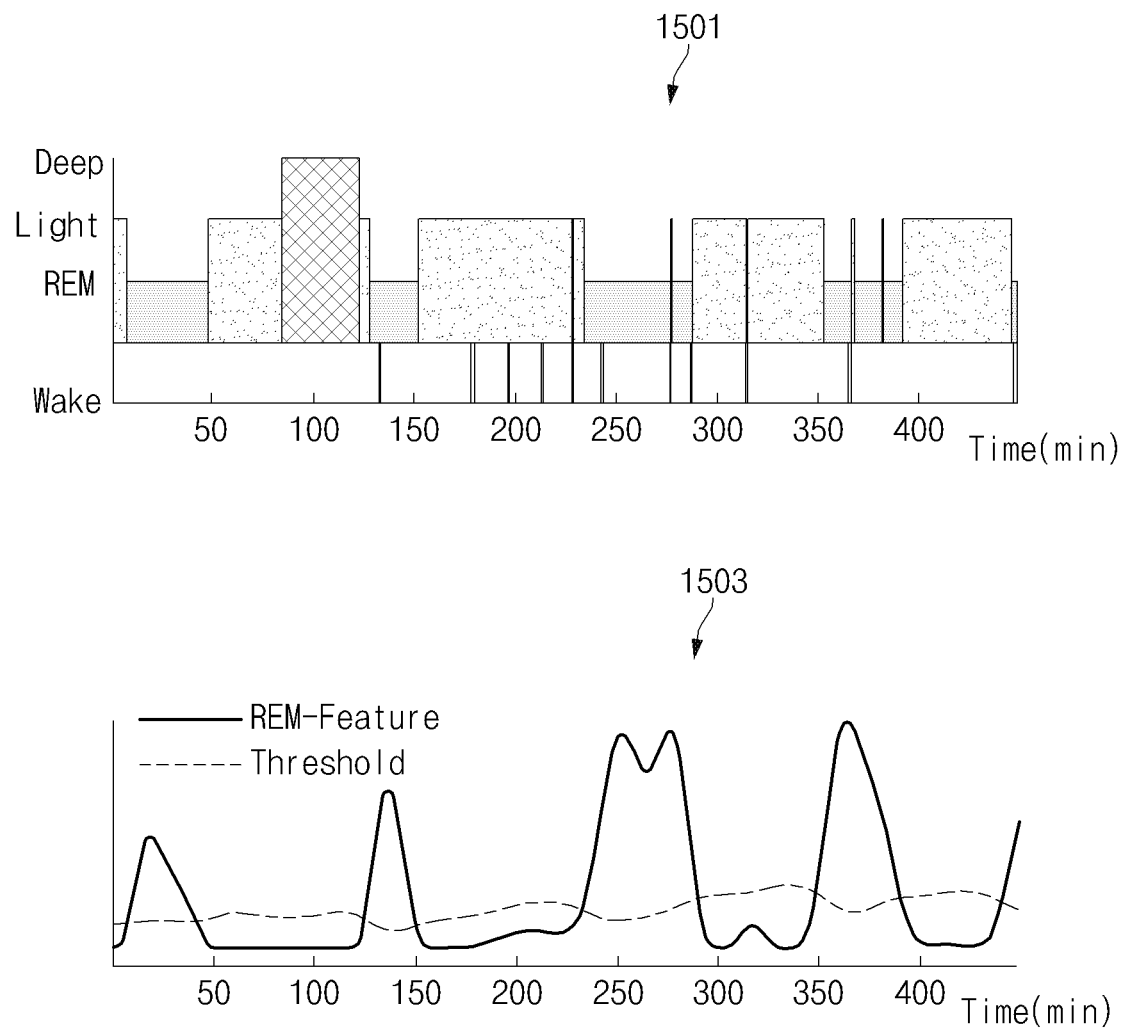
FIG. 15 illustrates a graph obtained by comparing an REM feature of a sleep pattern and a result of polysomnography.

FIG. 15 illustrates an REM feature of a sleep pattern and a result of measuring polysomnography.

A graph 1 1501 illustrates an REM sleep pattern as measured by polysomnography. A graph 2 1503 illustrates the estimated REM feature, using information about HR and HRV. In the graph 2 1503, the solid line may indicate the REM feature estimated by the electronic device (e.g., the electronic device 100 in FIG. 1), and the dotted line may indicate a specified threshold. An electronic device may set a specified threshold and may estimate a section where the estimated REM feature is greater than a specified threshold, as a REM sleep section.

When the graph 1 1501 is compared with the graph 2 1503, it may be seen that there is a relationship between the REM sleep section based on the polysomnography and the REM sleep section based on the estimated REM feature.

Accordingly, the electronic device may obtain a HR and/or HRV value and may estimate the REM sleep pattern based on the obtained HR and/or HRV value.

The electronic device may classify light sleep and deep sleep, using HR and/or HRV. Hereinafter, the classification of light sleep and deep sleep will be described.

The sleep may be divided into non-REM (NREM) sleep and REM sleep having the fast motion of a pupil. The NREM sleep may be divided into three sleep stages N1, N2, and N3 depending on the depth; the sleep obtained by combining N1 and N2 may be classified as light sleep; N3 may be classified as deep sleep or slow wave sleep. In summary, a change in autonomic nervous system during sleep has a feature of activating parasympathetic nerves in NREM sleep.

According to an embodiment, when estimating the sleep stage, an electronic device (e.g., a wrist-mounted wearable device) may use at least one of HR, HRV or a motion parameter (or actigraphy) in a method of distinguishing between light sleep and deep sleep.

Figure 16:
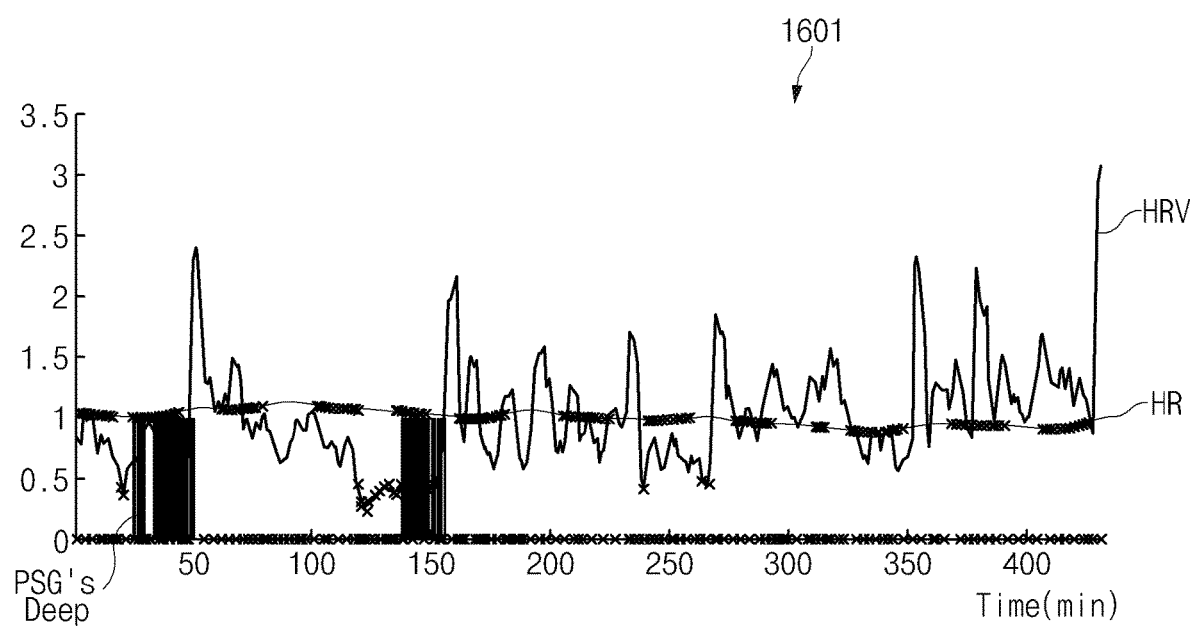
FIG. 16 illustrates an example of classifying sleep stages according to an embodiment.

FIG. 16 illustrates an example of sleep classification according to an embodiment.

According to an embodiment, an electronic device (e.g., the electronic device 100 of FIG. 1) may distinguish between light sleep and deep sleep, based on the actigraphy for measuring HR, HRV, and/or activity level (AL).

When the HRV is sufficiently low, when the HR is close to local minima, and/or when there is little motion, the electronic device may determine that an external object is in a deep sleep state.

A graph 1601 illustrates values obtained by measuring HR and HRV, and a deep sleep state section.

Referring to the graph 1601, the electronic device may determine that the external object is in a deep sleep state, when the values obtained by measuring HR and HRV satisfy the condition and there is no additionally-sufficient motion. In FIG. 16, the electronic device may determine that an external object is in a deep sleep state, between 30 and 50 minutes and between 140 and 150 minutes.

Figure 17:
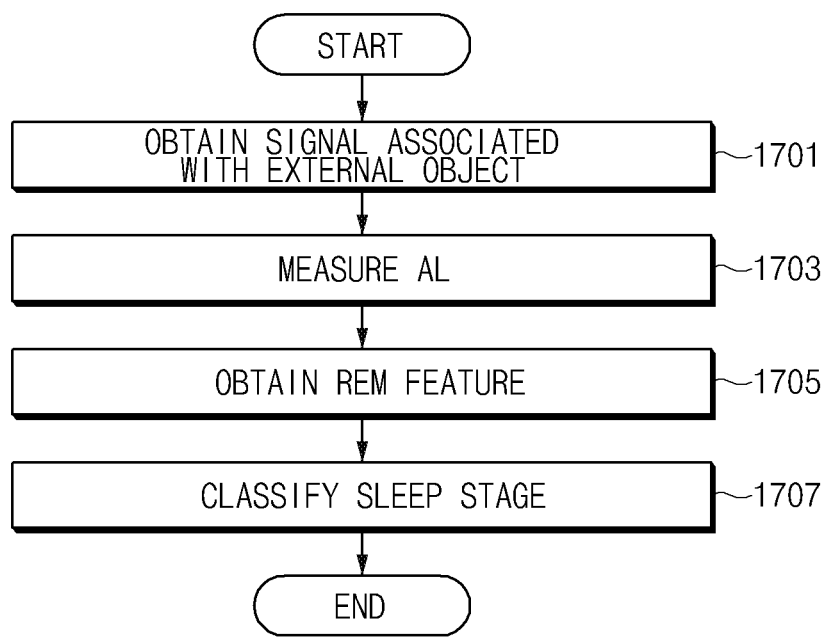
FIG. 17 is a flowchart of an operation of classifying sleep stages according to an embodiment.

FIG. 17 illustrates a method, in which an electronic device classifies a sleep stage, according to an embodiment.

According to an embodiment, an electronic device (e.g., the electronic device 100 of FIG. 1) may classify a sleep stage based on at least one of HR, HRV or a motion parameter (or actigraphy information). The measurement of HRV may use the method disclosed in the specification. The motion parameter according to an embodiment may correspond to a motion signal. For example, the motion parameter may be acceleration and/or derived motion-related information.

The electronic device may perform a sensing operation in operation 1701 and may analyze the result of performing the sensing operation in operation 1703 to operation 1707 to classify the sleep stage.

In operation 1701, the electronic device may obtain a signal associated with an external object. Afterward, the electronic device may process the signal associated with the external object. For example, the electronic device may process the motion signal and a biometric signal. The motion signal may be an acceleration signal; the biometric signal may be a PPG signal.

In operation 1703, the electronic device may measure an AL. The electronic device may measure the AL based on the acceleration signal.

In operation 1705, the electronic device may obtain an REM feature. The electronic device may calculate the REM feature based on, for example, HR and HRV. To this end, the electronic device may perform low-band filtering and Shannon entropy computation.

In operation 1707, the electronic device may classify the sleep stage. The electronic device may classify the sleep stage based on the REM feature. The electronic device may determine a sleep/wake state, may determine the REM, and may classify light sleep and deep sleep.

According to an embodiment, the electronic device may determine the sleep/wake state. The electronic device may compare the weighted sum of acceleration and a specified threshold. When the weighted sum is less than the specified threshold, the electronic device may determine a sleep state.

According to an embodiment, the electronic device may determine whether a current state is a REM sleep state. When the REM feature is greater than the specified threshold, the electronic device may determine that the current state is the REM sleep state.

According to an embodiment, the electronic device may classify the light sleep and the deep sleep. The electronic device may classify the light sleep and the deep sleep after determining the REM sleep. As such, the electronic device may classify the sleep stage based on HR, HRV and/or AL.

Figure 18:
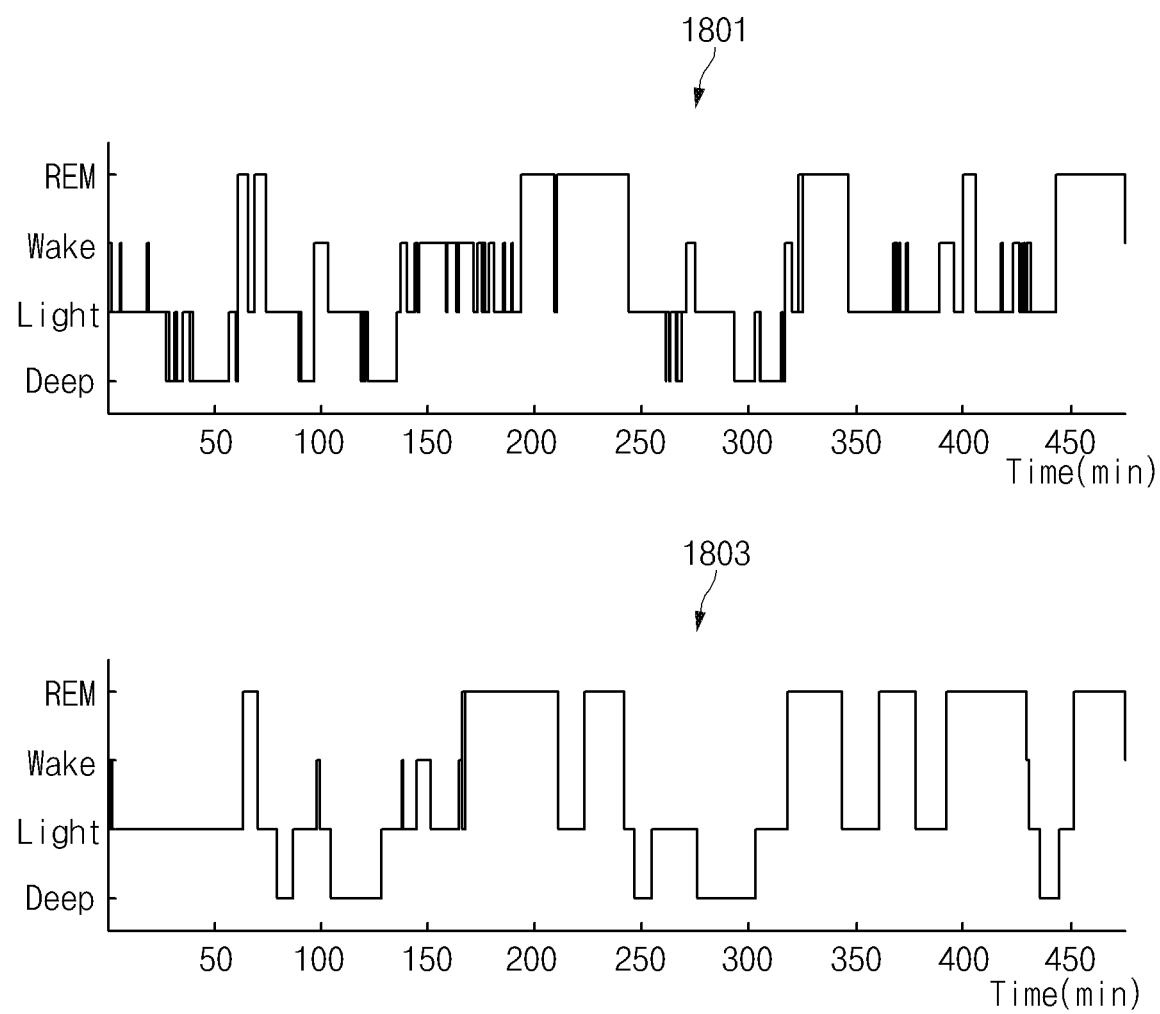
FIG. 18 illustrates a result of classifying sleep stages according to an embodiment.

FIG. 18 illustrates a result of classifying four stages of sleep according to an embodiment.

A graph 1 1801 illustrates a reference sleep step curve graph measured in polysomnography; a graph 2 1803 illustrates a sleep pattern measurement result estimated based on HR, HRV and/or a motion parameter according to an embodiment disclosed in the disclosure.

Referring to the graph 1 1801 and the graph 2 1803, it may be seen that there is a meaningful relationship between the sleep step curve graph and the sleep pattern measurement result according to an embodiment.

According to an embodiment disclosed in this specification, an electronic device (e.g., the electronic device 100 of FIG. 1) may include a detection circuit (e.g., the detection circuit 130 of FIG. 1) and a processor (e.g., the processor 110 of FIG. 1) operatively connected to the detection circuit. The processor may be configured to obtain a first signal associated with an external object through the detection circuit, to obtain a first heart rate (HR), using a first filter (e.g., the first trigger 330 of FIG. 3) having an attribute of a first frequency band and to obtain a second HR, using a second filter (e.g., the second tracker 340 of FIG. 3) having an attribute of a second frequency band, based at least on the first signal, to change at least some attributes associated with the second filter, based at least on the first HR and the second HR, and to obtain a second signal associated with the external object through the detection circuit, and generate heart rate variability (HRV) information, using the second filter, in which the at least some attributes are changed, based on the second signal.

According to an embodiment, the second frequency band may be a frequency band wider than the first frequency band.

According to an embodiment, the first filter and the second filter may be band pass filters.

According to an embodiment, the detection circuit may include at least one of a HR sensor (e.g., the sensor 132 of FIG. 1) or a communication circuit (e.g., the sensor 132 of FIG. 1) for transmitting or receiving a signal with an external electronic device.

According to an embodiment, the at least some attributes associated with the first filter may have fixed values.

According to an embodiment, the at least some attributes associated with the second filter may have values less than the at least some attributes associated with the first filter.

According to an embodiment, the at least some attributes may include at least one of a frequency band-related parameter ($\beta$) or a forgetting factor (smoothing factor, $\delta$).

According to an embodiment, the processor may be configured to obtain a correlation coefficient based on the first HR and the second HR, and to change the at least some attributes based on the correlation coefficient.

According to an embodiment, the processor may be configured to change the at least some attributes when the correlation coefficient satisfies a specified threshold.

According to an embodiment, the processor may be configured to change the at least some attributes based on correlation analysis.

According to an embodiment, the processor may be configured to change the at least some attributes based on phase synchronization or directionality analysis.

Moreover, according to an embodiment disclosed in this specification, an electronic device (e.g., the electronic device 100 of FIG. 1) may include a detection circuit (e.g., the detection circuit 130 of FIG. 1) and a processor (e.g., the processor 110 of FIG. 1) operatively connected to the detection circuit. The processor may be configured to obtain a first signal associated with an external object through the detection circuit, to obtain a first HR by using a first signal processing scheme and to obtain a second HR by using a second signal processing scheme based at least on the first signal, to change at least some attributes associated with the second signal processing scheme based at least on the first HR and the second HR, and to obtain a second signal associated with the external object through the HR sensor and to generate heart rate variability (HRV) information, using a second signal processing scheme in which the at least some attributes are changed.

According to an embodiment, the detection circuit may include at least one of a HR sensor (e.g., the sensor 132 of FIG. 1) or a communication circuit (e.g., the sensor 132 of FIG. 1) for transmitting or receiving a signal with an external electronic device.

According to an embodiment, the at least some attributes may include at least one of a frequency band-related parameter or a forgetting factor (smoothing factor).

According to an embodiment, the processor may be configured to obtain a correlation coefficient based on the first HR and the second HR, and to change the at least some attributes based on the correlation coefficient.

According to an embodiment, at least some attributes associated with the second signal processing scheme may have values less than the at least some attributes associated with the first signal processing scheme.

Furthermore, according to an embodiment disclosed in this specification, a method performed by an electronic device may include obtaining a signal associated with an external object, obtaining a first HR based on the signal, using a first signal processing scheme, obtaining a second HR based on the signal, using a second signal processing scheme, and generating HRV information based at least on the second HR.

According to an embodiment, the obtaining of the second HR may include obtaining at least some attribute values associated with the second signal processing scheme, based on the first HR and the second HR and obtaining the second HR based on the at least some attribute values, using the second signal processing scheme.

According to an embodiment, the generating of the HRV information may include generating the HRV information based on the second HR obtained based on the at least some attribute values.

According to an embodiment, the at least some attribute values associated with the second HR may be adaptively changed based on the first HR.

Figure 19:
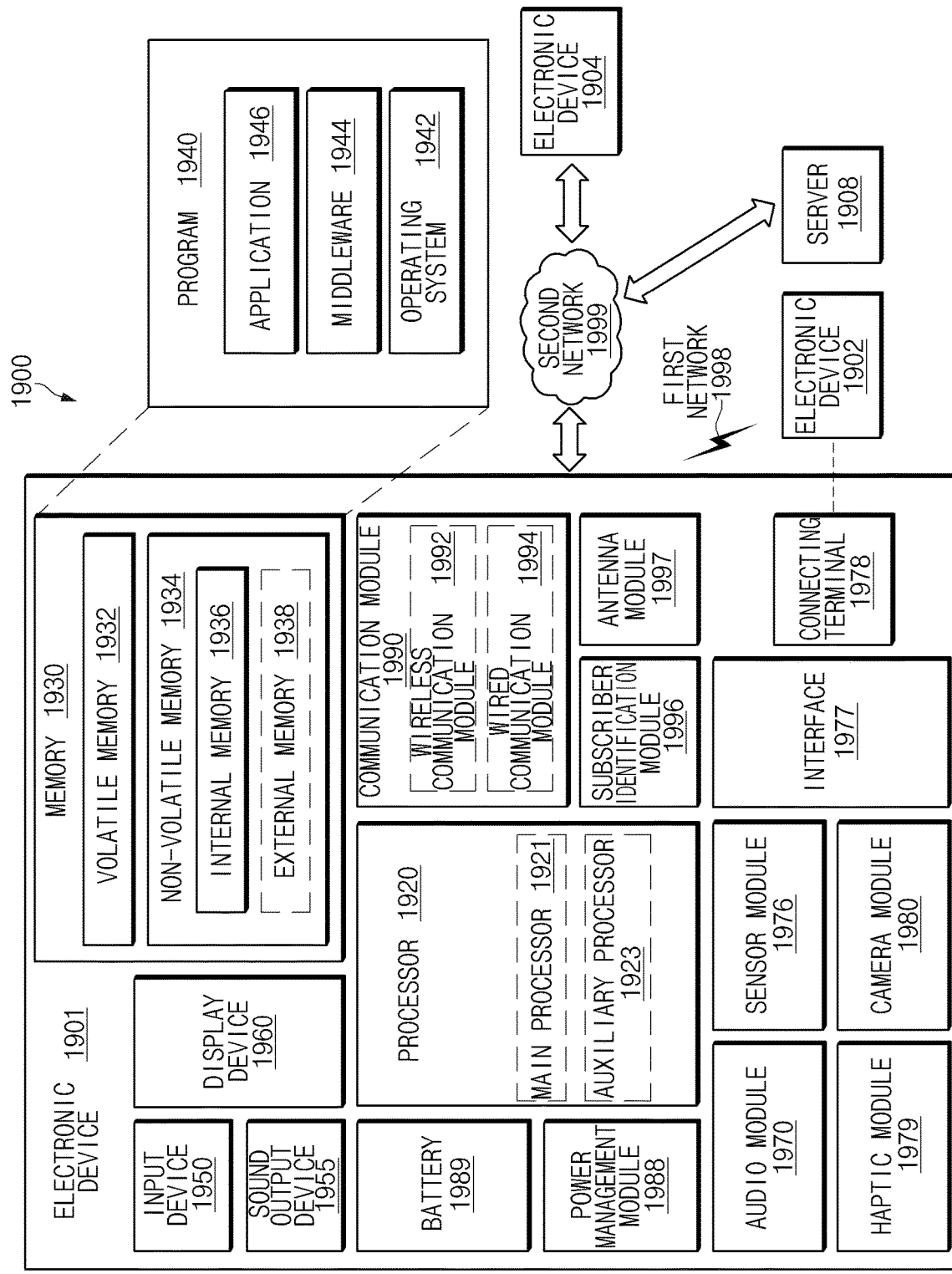
FIG. 19 is a block diagram of an electronic device for generating HRV information associated with an external object, using a plurality of filters in a network environment according to various embodiments.

FIG. 19 is a block diagram of an electronic device 1901 in a network environment 1900, according to various embodiments. Referring to FIG. 19, an electronic device 100 (e.g., the electronic device 100 of FIG. 1) may communicate with an electronic device 1902 through a first network 1998 (e.g., a short-range wireless communication) or may communicate with an electronic device 1904 or a server 1908 through a second network 1999 (e.g., a long-distance wireless communication) in the network environment 1900. According to an embodiment, the electronic device 1901 may communicate with the electronic device 1904 through the server 1908. According to an embodiment, the electronic device 1901 may include a processor 1920, a memory 1932, an input device 1950, a sound output device 1955, a display device 1960, an audio module 1970, a sensor module 1976, an interface 1977, a haptic module 1979, a camera module 1980, a power management module 1988, a battery 1989, a communication module 1990, a subscriber identification module 1996, and an antenna module 1997. In any embodiment, the electronic device 1901 may not include at least one (e.g., the display device 1960 or the camera module 1980) of the above-described components or may further include another component. In any embodiment, for example, as in the sensor module 1976 (e.g., a fingerprint sensor, an iris sensor, or an illuminance sensor) embedded in the display device 1960 (e.g., a display), some of components may be implemented integrally.

For example, the processor 1920 (e.g., the processor 110 of FIG. 1) may execute software (e.g., a program 1940) to control at least another component (e.g., hardware or software component) of the electronic device 1901 connected to the processor 1920, and may process and calculate various types of data. The processor 1920 may load commands or data received from other components (e.g., the sensor module 1976 or the communication module 1990) into a volatile memory 1932, may process the commands or the data, and may store the result data in a nonvolatile memory 1934. According to an embodiment, the processor 1920 may include a main processor 1921 (e.g., a central processing unit or an application processor) and an auxiliary processor 1923 (e.g., a graphic processing unit, an image signal processor, a sensor hub processor, or a communication processor), which is capable of operating independently and which, additionally or alternatively, uses lower power than the main processor 1921 or is specialized to a specified function. Herein, the auxiliary processor 1923 may be operated separately from the main processor 1921 or embedded in the main processor 1921.

In this case, the auxiliary processor 1923 may control at least part of the functions or states associated with at least one (e.g., the display device 1960, the sensor module 1976, or the communication module 1990) of the components of the electronic device 1901, instead of the main processor 1921 while the main processor 1921 is in an inactive (e.g., sleep) state or together with the main processor 1921 while the main processor 1921 is in an active (e.g., the execution of an application) state. According to an embodiment, the auxiliary processor 1923 (e.g., an image signal processor or a communication processor) may be implemented as some components of operatively associated other components (e.g., the camera module 1980 or the communication module 1990). The memory 1932 may store various pieces of data, for example, software (e.g., the program 1940) and input data or output data for commands associated with the software, which are used by at least one component (e.g., the processor 1920 or the sensor module 1976) of the electronic device 1901. The memory 1932 may include, for example, the volatile memory 1932 or the nonvolatile memory 1934.

The program 1940 may be software stored in the memory 1932 (e.g., the memory 120 of FIG. 1) and may include, for example, an operating system 1942, a middleware 1944, or an application 1946.

The input device 1950 may be a device for receiving commands or data to be used for the component (e.g., the processor 1920) of the electronic device 1901, from the outside (e.g., a user) of the electronic device 1901, and may include, for example, a microphone, a mouse, or a keyboard.

The sound output device 1955 may be a device for outputting an audio signal to the outside of the electronic device 1901; for example, the sound output device 1955 may include a speaker used for general purposes, such as multimedia playback or recording playback, and a receiver used only for receiving a call. According to an embodiment, the receiver may be implemented separately from the speaker or may be integrated with the speaker.

The display device 1960 may be a device for visually providing information to a user of the electronic device 1901 and may include, for example, a display, a hologram device, or a projector, and a control circuit for controlling a corresponding device. According to an embodiment, the display device 1960 may include a touch circuitry or a pressure sensor for measuring an intensity of pressure on the touch.

The audio module 1970 may convert a sound and an electric signal in dual directions. According to an embodiment, the audio module 1970 may obtain sound through the input device 1950, or may output sound through the sound output device 1955, or through an external electronic device (e.g., the electronic device 1902) (e.g., a speaker or a headphone) wiredly or wirelessly connected with the electronic device 1901.

The sensor module 1976 (e.g., the sensor 132 of FIG. 1) may generate an electrical signal or a data value corresponding to an internal operation state (e.g., power or a temperature) of the electronic device 1901 or corresponding to an external environment state. For example, the sensor module 1976 may include a gesture sensor, a gyro sensor, a barometric pressure sensor, a magnetic sensor, an acceleration sensor, a grip sensor, a proximity sensor, a color sensor, an infrared (IR) sensor, a biometric sensor, a temperature sensor, a humidity sensor, or an illumination sensor.

The interface 1977 may support a specified protocol capable of being connected to an external electronic device (e.g., the electronic device 1902) wiredly or wirelessly. According to an embodiment, the interface 1977 may include a high definition multimedia interface (HDMI), a universal serial bus (USB) interface, a secure digital (SD) card interface, or an audio interface.

A connecting terminal 1978 may include a connector capable of physically connecting the electronic device 1901 to an external electronic device (e.g., the electronic device 1902), for example, an HDMI connector, a USB connector, an SD card connector, or an audio connector. (e.g., a headphone connector).

The haptic module 1979 may convert an electrical signal to a mechanical stimulation (e.g., vibration or movement) or an electrical stimulation which the user may perceive through the sense of touch or the sense of movement. The haptic module 1979 may include, for example, a motor, a piezoelectric element, or an electric stimulator.

The camera module 1980 may shoot a still image or a video image. According to an embodiment, the camera module 1980 may include one or more lenses, an image sensor, an image signal processor, or a flash.

The power management module 1988 may be a module for managing power supplied to the electronic device 1901 and may serve as at least a part of a power management integrated circuit (PMIC).

The battery 1989 that is a device for supplying power to at least one component of the electronic device 1901 may include, for example, a primary cell incapable of being recharged, a secondary cell rechargeable, or a fuel cell.

The communication module 1990 (e.g., the communication circuit 140 of FIG. 1) may establish a wired or wireless communication channel between the electronic device 1901 and an external electronic device (e.g., the electronic device 1902, the electronic device 1904, or the server 1908) and may perform communication through the established communication channel. The communication module 1990 may include at least one communication processor operating independently from the processor 1920 (e.g., an application processor) and supporting the wired communication or the wireless communication. According to an embodiment, the communication module 1990 may include a wireless communication module 1992 (e.g., a cellular communication module, a short-range wireless communication module, or a global navigation satellite system (GNSS) communication module) or a wired communication module 1994 (e.g., a local area network (LAN) communication module or a power line communication module). The communication module 1990 may communicate with an external electronic device through the first network 1998 (e.g., a short-range communication network such as Bluetooth, Wi-Fi direct or infrared data association (IrDA)) or the second network 1999 (e.g., a long-range communication network such as a cellular network, Internet, or a computer network (e.g., LAN or WAN)), using the corresponding communication module among the wireless communication module 1992 or the wired communication module 1994. The above-mentioned various communication modules 1990 may be implemented into one chip or into separate chips, respectively.

According to an embodiment, the wireless communication module 1992 may distinguish and authenticate the electronic device 1901 in the communication network, using user information stored in the subscriber identification module 1996.

The antenna module 1997 may include one or more antennas for transmitting or receiving a signal or power to or from the outside. According to an embodiment, the communication module 1990 (e.g., the wireless communication module 1992) may transmit a signal to an external electronic device through an antenna suitable for a communication method, or may receive a signal from the external electronic device.

At least part of the components may be connected to each other through a communication scheme (e.g., a bus, a general purpose input and output (GPIO), a serial peripheral interface (SPI), or a mobile industry processor interface (MIPI)) between peripheral devices and may exchange signals (e.g., commands or data) with each other.

According to an embodiment, the command or data may be transmitted or received between the electronic device 1901 and the external electronic device 1904 through the server 1908 connected to the second network 1999. Each of the electronic devices 1902 and 1904 may be a device of which the type is different from or the same as that of the electronic device 1901. According to an embodiment, all or part of operations that the electronic device 1901 will perform may be executed by another external electronic device or a plurality of external electronic devices. According to an embodiment, when the electronic device 1901 needs to execute any function or service automatically or in response to a request, the electronic device 1901 may not perform the function or the service internally, but, alternatively or additionally, it may make a request for at least part of a function associated with the electronic device 1901 to the external electronic device. The external electronic device receiving the request may execute the requested function or additional function and may transmit the execution result to the electronic device 1901. The electronic device 1901 may provide the requested function or service by processing the received result as it is, or additionally. To this end, for example, cloud computing, distributed computing, or client-server computing technologies may be used.

According to various embodiments disclosed in the disclosure, the electronic device may include various types of devices. For example, the electronic device may include at least one of a portable communication device (e.g., a smartphone), a computer device, a portable multimedia device, a mobile medical appliance, a camera, a wearable device, or a home appliance. An electronic device according to an embodiment of the disclosure may not be limited to the above-described electronic devices.

Various embodiments of the disclosure and terms used herein are not intended to limit the technologies described in the disclosure to specific embodiments, and it should be understood that the embodiments and the terms include modification, equivalent, and/or alternative on the corresponding embodiments described herein. With regard to description of drawings, similar components may be marked by similar reference numerals. The terms of a singular form may include plural forms unless otherwise specified. In the disclosure disclosed herein, the expressions "A or B", "at least one of A and/or B", "A, B, or C", or "at least one of A, B, and/or C", and the like used herein may include any and all combinations of one or more of the associated listed items. Expressions such as "first," or "second," and the like, may express their components regardless of their priority or importance and may be used to distinguish one component from another component but is not limited to these components. When an (e.g., first) element is referred to as being "(operatively or communicatively) coupled with/to" or "connected to" another (e.g., second) element, it may be directly coupled with/to or connected to the other element or an intervening element (e.g., a third element) may be present.

The term "module" used herein may include a unit, which is implemented with hardware, software, or firmware, and may be interchangeably used with the terms "logic", "logical block", "part", "circuit", or the like. The "module" may be a minimum unit of an integrated part or a part thereof or may be a minimum unit for performing one or more functions or a part thereof. For example, the module may be implemented with an application-specific integrated circuit (ASIC).

Various embodiments of the disclosure may be implemented with software (e.g., the program 1940) including instructions stored in machine-readable storage media (e.g., an internal memory 1936 or an external memory 1938) readable by a machine (e.g., a computer). The machine may be a device capable of calling the stored instructions from the storage media and capable of operating depending on the called instructions and may include an electronic device (e.g., the electronic device 1901) according to the disclosed embodiments. The instructions, when executed by a processor (e.g., the processor 1920), may cause the processor to perform a function corresponding to the instructions, directly or by using other components under the control of the processor. The instructions may include the code generated or executed by a compiler or an interpreter. The machine-readable storage medium may be provided in the form of a non-transitory storage medium. Herein, 'non-transitory' just means that the storage medium is a tangible device and does not include a signal, and 'non-transitory' does not distinguish between the case where data is semi-permanently stored in the storage medium and the case where the data is stored temporarily.

According to an embodiment, a method according to various embodiments disclosed herein may be provided to be included in a computer program product. The computer program product may be traded between a seller and a buyer as a product. The computer program product may be distributed, in the form of a machine-readable storage medium (e.g., compact disc read only memory (CD-ROM)) or online through an application store (e.g., PlayStore™). In the case of on-line distribution, at least part of the computer program product may be at least temporarily stored in the storage medium such as the memory of a manufacturer's server, an application store's server, or a relay server or may be generated temporarily.

Each of components (e.g., a module or a program) according to various embodiments may include a single entity or a plurality of entities; some of the above-described corresponding sub components may be omitted, or any other sub component may be further included in various embodiments. Alternatively or additionally, some components (e.g., a module or a program) may be combined with each other so as to form one entity, so that the functions of the components may be performed in the same manner as before the combination. According to various embodiments, operations executed by modules, program modules, or other components may be executed by a successive method, a parallel method, a repeated method, or a heuristic method. Alternatively, at least some of the operations may be executed in another order or may be omitted, or any other operation may be added.

What is claimed is:

1. An electronic device comprising:
a detection circuit; and
a processor operatively connected to the detection circuit, wherein the processor is configured to:
obtain a first signal associated with an external object through the detection circuit;
identify a first heart rate (HR), using a first filter having an attribute of a first frequency band and identify a second HR, using a second filter having an attribute of a second frequency band, based at least on the first signal;
change at least one attribute associated with the second filter, based at least on the first HR and the second HR;
obtain a second signal associated with the external object through the detection circuit;
identify a third HR, using the second filter having the changed at least one attribute, based on the second signal; and
generate heart rate variability (HRV) information based on the third HR.

2. The electronic device of claim 1, wherein the first filter having the attribute of the first frequency band and the second filter having the attribute of the second frequency band are band pass filters, and the second frequency band is a frequency band wider than the first frequency band.

3. The electronic device of claim 1, wherein the detection circuit includes at least one of a HR sensor or a communication circuit for transmitting or receiving a signal with an external electronic device.

4. The electronic device of claim 1, wherein at least one attribute associated with the first filter has fixed values.

5. The electronic device of claim 4, wherein the at least one attribute associated with the second filter has values less than the at least one attribute associated with the first filter.

6. The electronic device of claim 1, wherein the at least one attribute includes at least one of a frequency band-related parameter or a forgetting factor.

7. The electronic device of claim 1, wherein the processor is configured to:
obtain a correlation coefficient based on the first HR and the second HR; and
change the at least one attribute based on the correlation coefficient.

8. The electronic device of claim 7, wherein the processor is configured to:
when the correlation coefficient satisfies a specified threshold, change the at least one attribute.

9. The electronic device of claim 1, wherein the processor is configured to:
change the at least one attribute based on correlation analysis.

10. The electronic device of claim 9, wherein the processor is configured to:
change the at least one attribute based on phase synchronization or directionality analysis.

11. A method performed by an electronic device, the method comprising:
obtaining a first signal associated with an external object;
identifying a first HR based on the first signal, using a first filter having an attribute of a first frequency band;
identifying a second HR based on the first signal, using a second filter having an attribute of a second frequency band;
changing at least one attribute associated with the second filter, based at least on the first HR and the second HR;
obtaining a second signal associated with the external object;
identifying a third HR using the second filter having the changed at least one attribute based on the second signal; and
generating HRV information based at least on the third HR.

12. The method of claim 11, wherein the first filter having the:
attribute of the first frequency band and the second filter having the attribute of the second frequency band are band pass filters, and the second frequency band is a frequency band wider than the first frequency band.

13. The method of claim 12, wherein the at least one attribute associated with the second HR is adaptively changed based on the first HR.

* * * * *